(12) United States Patent
Ouellette

(10) Patent No.: US 11,806,720 B2
(45) Date of Patent: Nov. 7, 2023

(54) PROBE ASSEMBLY AND METHOD FOR SECURING AND INSERTING A PROBE

(71) Applicant: Global Life Sciences Solutions USA LLC, Marlborough, MA (US)

(72) Inventor: Matthew Ouellette, Marlborough, MA (US)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 583 days.

(21) Appl. No.: 16/956,990

(22) PCT Filed: Dec. 19, 2018

(86) PCT No.: PCT/EP2018/085817
§ 371 (c)(1),
(2) Date: Jun. 22, 2020

(87) PCT Pub. No.: WO2019/129570
PCT Pub. Date: Jul. 4, 2019

(65) Prior Publication Data
US 2020/0346220 A1    Nov. 5, 2020

Related U.S. Application Data

(60) Provisional application No. 62/611,282, filed on Dec. 28, 2017.

(51) Int. Cl.
*B01L 9/00* (2006.01)
*C12M 1/00* (2006.01)
*C12M 1/12* (2006.01)

(52) U.S. Cl.
CPC .............. *B01L 9/00* (2013.01); *C12M 23/14* (2013.01); *C12M 37/00* (2013.01);
(Continued)

(58) Field of Classification Search
CPC . C12M 23/14; C12M 37/00; B01L 2200/025; B01L 9/00; B01L 2200/0689;
(Continued)

(56) References Cited

U.S. PATENT DOCUMENTS

| 7,927,316 B2 | 4/2011 | Proulx et al. |
| 2005/0229727 A1* | 10/2005 | Caderas ................ F15B 15/261 |
| | | 73/866.5 |
| 2014/0260712 A1 | 9/2014 | Damren et al. |

FOREIGN PATENT DOCUMENTS

| WO | 8303778 A1 | 11/1983 |
| WO | 2017/091635 A1 | 6/2017 |

OTHER PUBLICATIONS

PCT International Search Report and Written Opinion for PCT Application No. PCT/EP2018/085817 dated Apr. 8, 2019 (15 pages).
(Continued)

*Primary Examiner* — Anshu Bhatia
(74) *Attorney, Agent, or Firm* — Eversheds Sutherland (US) LLP

(57) ABSTRACT

A probe assembly for inserting a probe into a vessel or tubing includes a probe sheath having a proximal end and a distal end and being configured for operative coupling to a vessel or tubing, the probe sheath being configured to receive a probe and to permit movement of the probe towards the distal end of the probe sheath, and a locking mechanism configured to restrain longitudinal movement of the probe with respect to the sheath in a locked state. The locking mechanism may be unlocked to allow for movement of the probe with respect to the sheath.

25 Claims, 15 Drawing Sheets

(52) U.S. Cl.
CPC . *B01L 2200/025* (2013.01); *B01L 2200/0689* (2013.01); *B01L 2200/141* (2013.01); *B01L 2200/147* (2013.01); *B01L 2300/123* (2013.01)

(58) Field of Classification Search
CPC ......... B01L 2200/141; B01L 2200/147; B01L 2300/123
See application file for complete search history.

(56) References Cited

OTHER PUBLICATIONS

European Office Action for EP Application No. 18826326.3, dated May 31, 2023 (10 pages).

\* cited by examiner

PROBE ASSEMBLY AND METHOD FOR SECURING AND INSERTING A PROBE

CROSS REFERENCE TO RELATED APPLICATIONS

This application claims the priority benefit of PCT/EP2018/085817 filed on Dec. 19, 2018, which claims priority benefit of U.S. Provisional Patent Application No. 62/611,282 filed on Dec. 28, 2017, the entire contents of which are hereby incorporated by reference herein.

BACKGROUND

Technical Field

Embodiments of the invention relate generally to bioprocessing systems and methods and, more particularly, to systems and methods for inserting sensors into bioreactors vessels and tubing, including flexible or semi-rigid bags or tubing.

Discussion of Art

A variety of vessels, devices, components and unit operations are known for carrying out biochemical and/or biological processes and/or manipulating liquids and other products of such processes. Increasingly, in order to avoid the time, expense, and difficulties associated with sterilizing the vessels used in biopharmaceutical manufacturing processes, single-use or disposable bioreactor bags and single-use mixer bags are used as such vessels. For instance, biological materials (e.g., animal and plant cells) including, for example, mammalian, plant or insect cells and microbial cultures can be processed using disposable or single-use mixers and bioreactors.

The manufacturing of complex biological products such as proteins (e.g., monoclonal antibodies, peptides, hormones, and vaccine immunogens) requires, in many instances, multiple processing steps ranging from cell culture (bacteria, yeast, insect, fungi, etc.) and/or fermentation, to primary recovery, purification, and others. Conventional bioreactor-based manufacturing of biological products generally utilizes batch, or fed-batch processing through a series of unit operations with subsequent off-line laboratory analysis conducted on representative samples collected from various points of the process to ensure quality.

In order to obtain timely information regarding changing conditions within a bioreactor vessel during its operation, the use of sensor technology has been employed. With regard to use of disposable bioreactors, there are recognized difficulties in sterilely inserting a sensor into a flexible-walled bioreactor or flexible tubing that feeds or drains such vessels. For example, optical, electrical, and pH sensors, positioned inside a flexible bag or tubing require an attachment means that allows for a clear signal to be communicated to or from external analytical instrumentation.

Existing sensor assemblies typically use a bellows-type, flexible sheath through which a long probe is inserted, as disclosed, for example, in U.S. Pat. No. 7,901,934. With these assemblies, however, nothing constrains axial movement of the probe relative to the sheath, meaning that accidental movement of the probe prior to insertion into a bioprocessing container can perforate or puncture the membrane on the end of the assembly that serves as a sterile bather. In addition, with existing probe assemblies, insertion depth can vary from one bioprocessing container to the next, and even within a discrete manufacturing or cell cultivation process, due to the unconstrained movement between the sheath and the probe, which can lead to variations in, or imprecise, sensor readouts. Moreover, certain existing assemblies require deflection of the connector or port attached to the vessel or bag in order to position the probe for angled insertion, which adds complexity to the assembly and increases the possibility of rupture or tears in the system which could taint the product.

In view of the above, there is a need for a probe assembly and method for securing and sterilely inserting a probe into a flexible bag or tubing which prevents inadvertent axial translation of the probe to mitigate the possibility of compromising sterility, and provides for a consistent, reliable and repeatable insertion depth.

BRIEF DESCRIPTION

In an embodiment, a probe assembly for inserting a probe into a vessel or tubing includes a probe sheath having a proximal end and a distal end and being configured for operative coupling to a vessel or tubing, the probe sheath being configured to receive a probe and to permit movement of the probe towards the distal end of the probe sheath, and a locking mechanism configured to restrain longitudinal movement of the probe with respect to the sheath in a locked state. The locking mechanism may be unlocked to allow for movement of the probe with respect to the sheath.

In another embodiment, a method of aseptically inserting a probe into a vessel or tubing is provided. The method includes the steps of coupling a connector assembly to a probe sheath, engaging a locking mechanism with a plunger received by the probe sheath to restrain axial movement of the plunger within the probe sheath, inserting a probe through the plunger and into the probe sheath, and connecting the probe sheath to a port in the vessel or tubing via the connector assembly.

In yet another embodiment, a probe assembly for inserting a probe into a vessel or tubing, is provided. The assembly includes a probe sheath having a proximal end and a distal end and being configured for operative coupling to a vessel or tubing, the probe sheath being configured to receive a probe and to permit movement of the probe towards the distal end of the probe sheath, a plunger slidably received within the probe sheath, the plunger being configured to sealingly engage the probe sheath and the probe, and a latch mechanism configured to restrain movement of the probe with respect to the probe sheath after deployment of the probe into the vessel or tubing and to maintain the probe at a predetermined insertion depth.

DRAWINGS

The present invention will be better understood from reading the following description of non-limiting embodiments, with reference to the attached drawings, wherein below:

DETAILED DESCRIPTION

Figure 1:
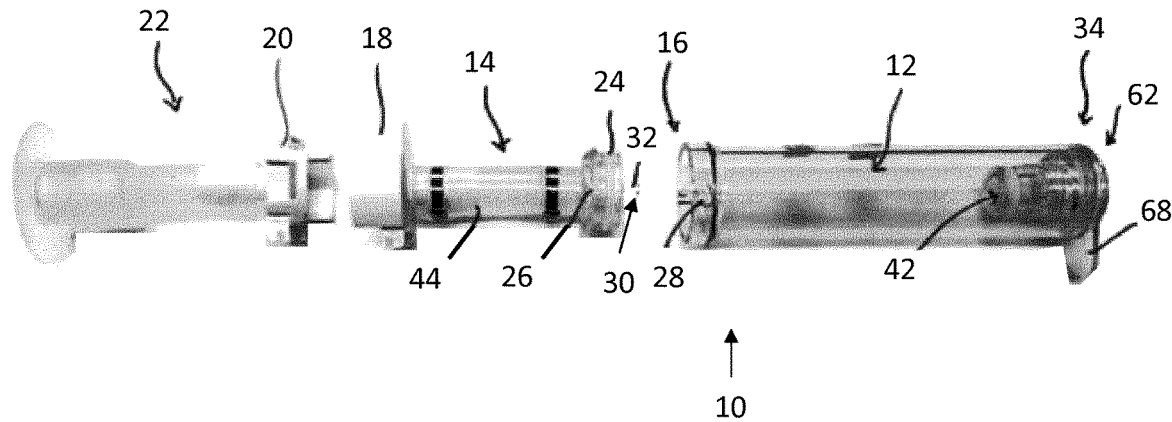
FIG. 1 is a partial exploded, perspective view of a probe assembly according to an embodiment of the invention.

Reference will be made below in detail to exemplary embodiments of the invention, examples of which are illustrated in the accompanying drawings. Wherever possible, the same reference characters used throughout the drawings refer to the same or like parts.

As used herein, the term "flexible" refers to a structure or material that is pliable, or capable of being bent without breaking, and may also refer to a material that is compressible or expandable. An example of a flexible structure is a bag formed of polyethylene film. The terms "rigid" and "semi-rigid" are used herein interchangeably to describe structures that are "non-collapsible," that is to say structures that do not fold, collapse, or otherwise deform under normal forces to substantially reduce their elongate dimension. "Collapsible" is defined to include substantially flexible material that will fold onto or into itself, such as, for example, fabrics and materials that form pleated or "accordion-like" structures, such as bellows, in response to a compressive force. Depending on the context, "semi-rigid" can also denote a structure that is more flexible than a "rigid" element, e.g., a bendable tube or conduit, but still one that does not collapse longitudinally under normal conditions and forces.

A "vessel," as the term is used herein, means a flexible bag, a flexible container, a semi-rigid container, a rigid container, or a flexible or semi-rigid tubing, as the case may be. The term "vessel" as used herein is intended to encompass bioreactor vessels having a wall or a portion of a wall that is flexible or semi-rigid, single use flexible bags, as well as other containers or conduits commonly used in biological or biochemical processing, including, for example, cell culture/purification systems, mixing systems, media/buffer preparation systems, and filtration/purification systems, e.g., chromatography and tangential flow filter systems, and their associated flow paths. As used herein, the term "bag" means a flexible or semi-rigid container, vessel, or tubing used, for example, as a bioreactor or mixer for the contents within.

Typically, a flexible bag used for mixing or bioprocessing is supported by a rigid support structure or supported within a rigid vessel. A probe assembly according to an embodiment of the invention is particularly useful for attaching to a disposable or single use flexible bioreactor or mixer bag, or a flexible tubing. Sterilizing a probe before it is inserted into a reactor bag or vessel is often essential. When the probe is inserted via a probe assembly, it may be necessary to sterilize the entire probe assembly, including any sheaths, connectors, and tubes, as well as the probe itself, prior to inserting the probe into the reactor vessel. Common methods of sterilization include, but are not limited to, autoclaving, radiation treatment, and chemical treatment. When an autoclave is used, it can be important for steam to reach all of the interior surfaces of a probe assembly, as well as the exterior portions.

A typical industry standard size sensor is about 12 mm diameter×225 mm long, but any size sensor can be used. The sensor can be installed as an elongate probe body that is configured to be advanced into the vessel via a probe sheath. This is particularly advantageous when the vessel has a flexible or non-rigid form. A connector is commonly used to perform the aseptic connection between the probe sheath assembly and the sterile vessel.

Aseptic and other connectors typically are two-part constructions (either a male and matching female part or a pair of "genderless" parts) that are joined together. One part of the aseptic connect can be joined to the vessel, e.g., by a suitable sized length of tubing. This connector is then coupled to a corresponding connector part on the probe assembly, as described below. When the connector that is mounted on the container is connected to the connector on the sterilized probe sheath assembly, a sterile passageway is formed between the container and the probe sheath, a passageway through which a sterile sensor or probe can be inserted such that it can take measurements of conditions inside the vessel.

Referring to FIGS. 1-4, a probe assembly 10 according to an embodiment of the invention is illustrated. The probe assembly 10 includes a generally hollow probe sheath 12. In an embodiment, the probe sheath 12 has an elongate, cylindrical body extending between a proximal end 34 and a distal end 16, and has an inner cylindrical surface defining a passageway 48 therethrough. The sheath may be opaque or transparent, and may include one or more windows that allow for viewing the interior of the sheath. The probe assembly 10 further includes a connector assembly 14 removably connected to the probe sheath 12 at the distal end 16 thereof. The connector assembly 14 includes a connector mating portion 18 at a distal end of the connector assembly which is configured to interface with or connect to a corresponding connector mating portion 20 of a connector 22 attached to the wall of a bag, as discussed hereinafter. As illustrated in FIGS. 1-4, a proximal end of the connector assembly 14 includes an O-ring 24 that is dimensioned so as to sealingly engage the interior wall of the probe sheath 12. In an embodiment, the connector assembly 14 may be removably connected to the probe sheath 12 through a bayonet mounting mechanism, although other connection means enabling the removable attachment of the connector portion 14 to the probe sheath 12 may be utilized without departing from the broader aspects of the invention. As illustrated in FIG. 1, for example, the proximal end of the connector assembly 14 may have one or more radial pins or lugs 26 that are received by corresponding slots 28 in the distal end 16 of the probe sheath 12. As also shown in FIGS. 1-4, a proximal end of the connector assembly 14 includes a latch mechanism 30, the purpose of which will be discussed hereinafter. In an embodiment, the latch mechanism 30 may include two spaced-apart, resilient arms 32 that extend axially into the hollow interior of the probe sheath 12 when the connector assembly 14 is coupled to the probe sheath 12.

Figure 2:
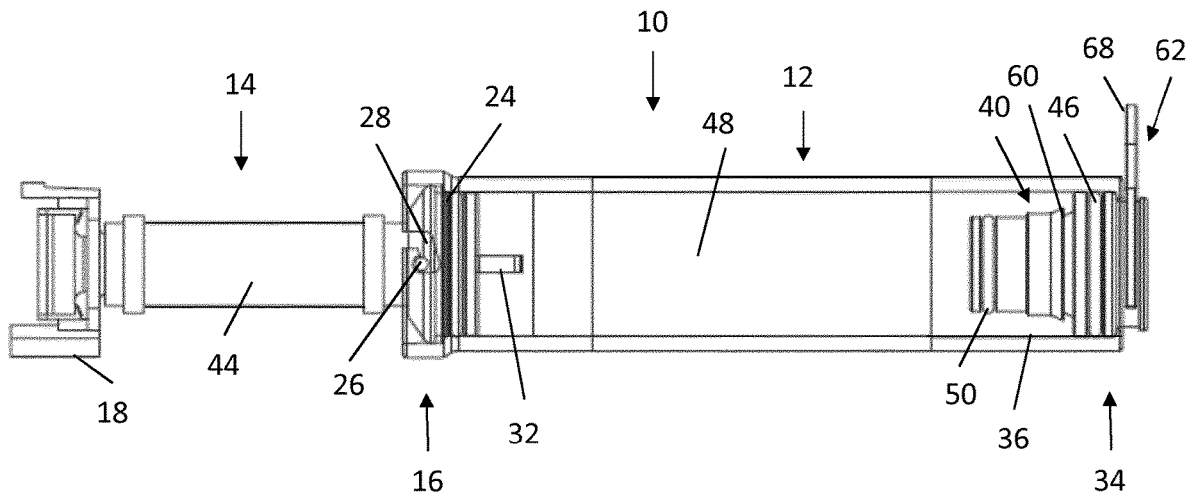
FIG. 2 is a top plan view of the probe assembly of FIG. 1, prior to coupling to a bag or tubing.
Figure 3:
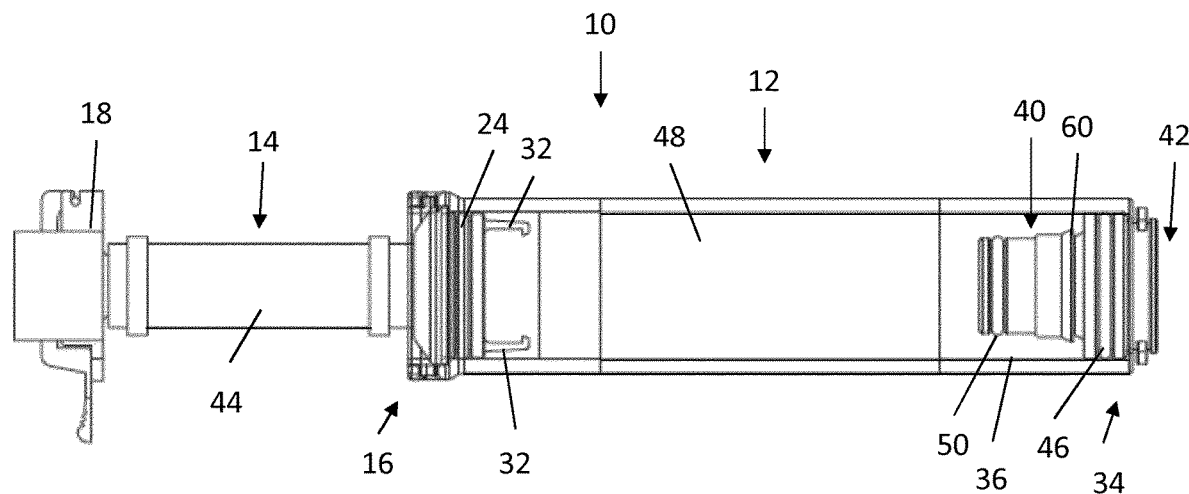
FIG. 3 is a side elevational view of the probe assembly of FIG. 1, prior to coupling to a bag or tubing.
Figure 4:
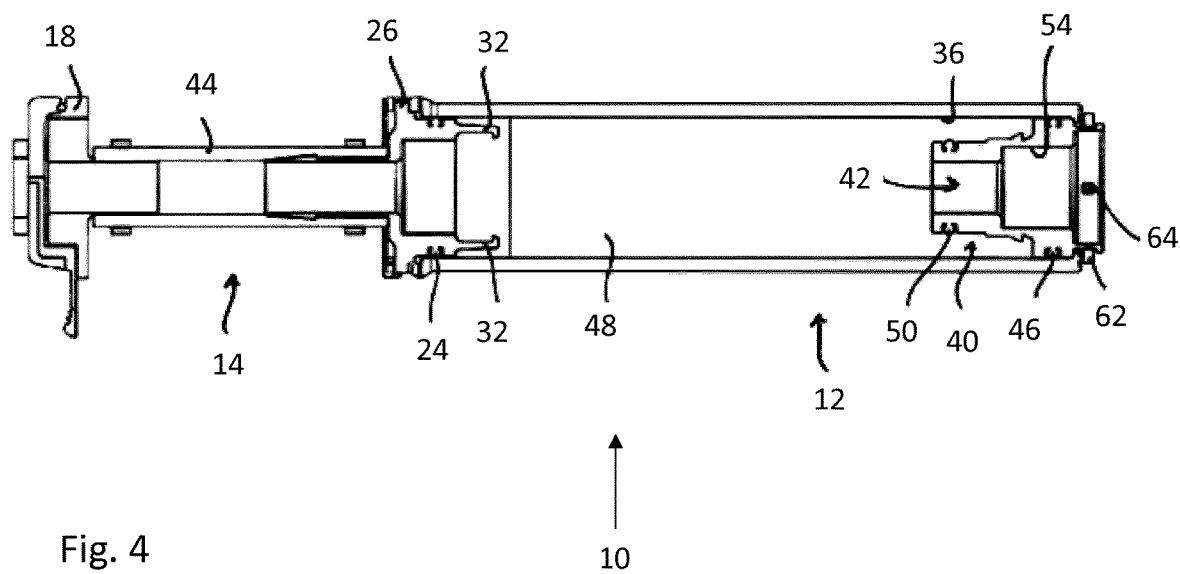
FIG. 4 is a cross-sectional side view of the probe assembly of FIG. 1, prior to coupling to a bag or tubing.
Figure 5:
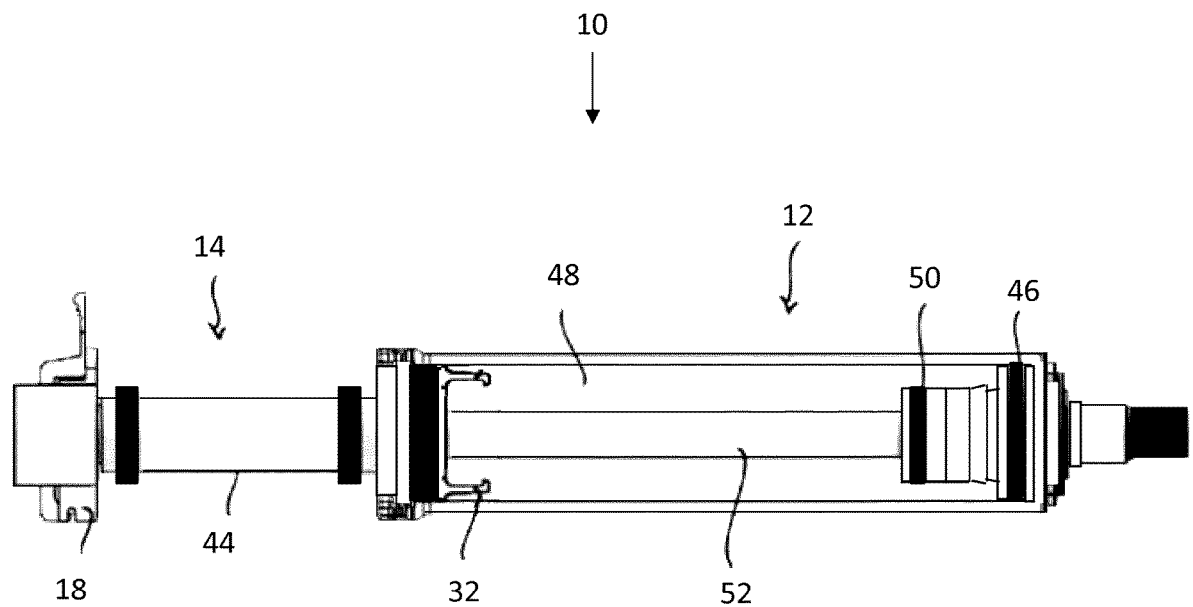
FIG. 5 is a side elevational view of the probe assembly of FIG. 1, shown with a probe in secured position and prior to coupling to a bag or tubing.
Figure 6:
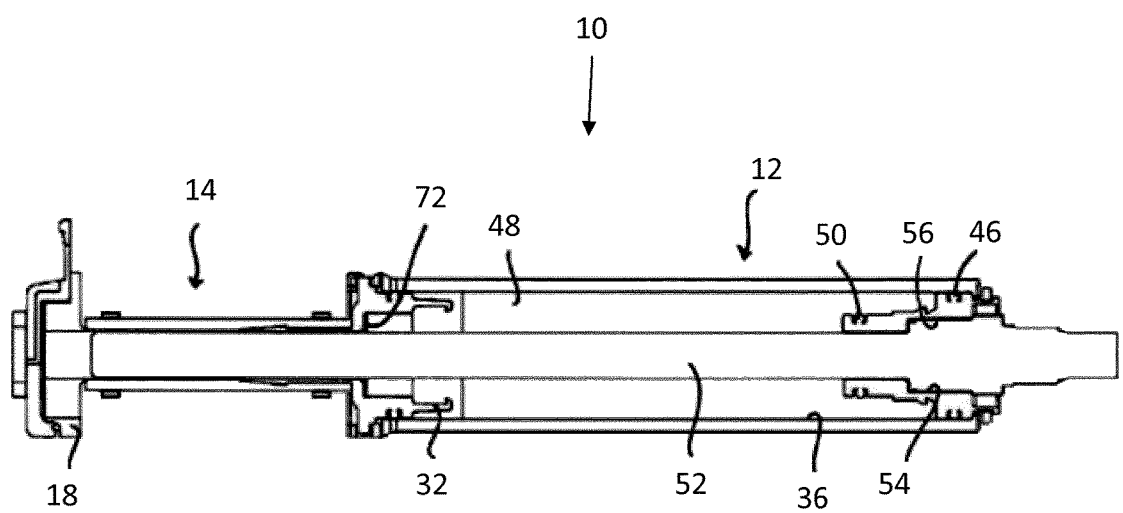
FIG. 6 is a cross-sectional side view of the probe assembly of FIG. 1, shown with the probe in secured position and prior to coupling to a bag or tubing.

With further reference to FIGS. 1-4, a second end 34 of the probe sheath 12 provides an opening 36 into which a plunger 40 is slidably received. As shown in FIGS. 2-4, a seal 46 exists between the inside of the probe sheath 12 and the outside of the probe sheath plunger 40 which allows relative movement between the probe sheath 12 and the probe sheath plunger 40. The seal 46 between the probe sheath 12 and the probe sheath plunger 40 is configured so that the seal 46 will provide a sterile bather between the volume 48 inside the probe sheath assembly 12 and the outside of the probe sheath 12 when the probe sheath 12 is sterilized. A second seal element 50 is provided on a distal end of the plunger 40, for forming a seal with a proximal end of the connector assembly 14 when the probe is deployed into a bag or tube, as discussed hereinafter.

As best shown in FIGS. 4-7, the plunger 40 has an opening 42 into which the sensor or probe body 52 can be inserted and secured such that a seal is formed between the sensor or probe 52 and the probe sheath plunger 40, to maintain sterile or aseptic conditions within the internal volume 48. In an embodiment, a portion 54 of the opening 42 is formed with a plurality of threads for engaging a corresponding threaded portion 56 of the probe 52, although other attachment means may also be utilized without departing from the broader aspects of the invention. The plunger 40 may also include an O-ring or like sealing element for forming a seal with the probe 52 to maintain a sterile or aseptic environment within the internal volume 48.

As best shown in FIGS. 2-11, the plunger 40 also includes an annular flange 60 having a diameter that generally corresponds to a distance between the resilient arms 32 on the connector assembly 14. The resilient arms 32 and flange 60 collectively form the latch mechanism 30, which provides for a reliable and repeatable probe insertion depth and audible indication of proper probe deployment, as discussed hereinafter.

Figure 13:
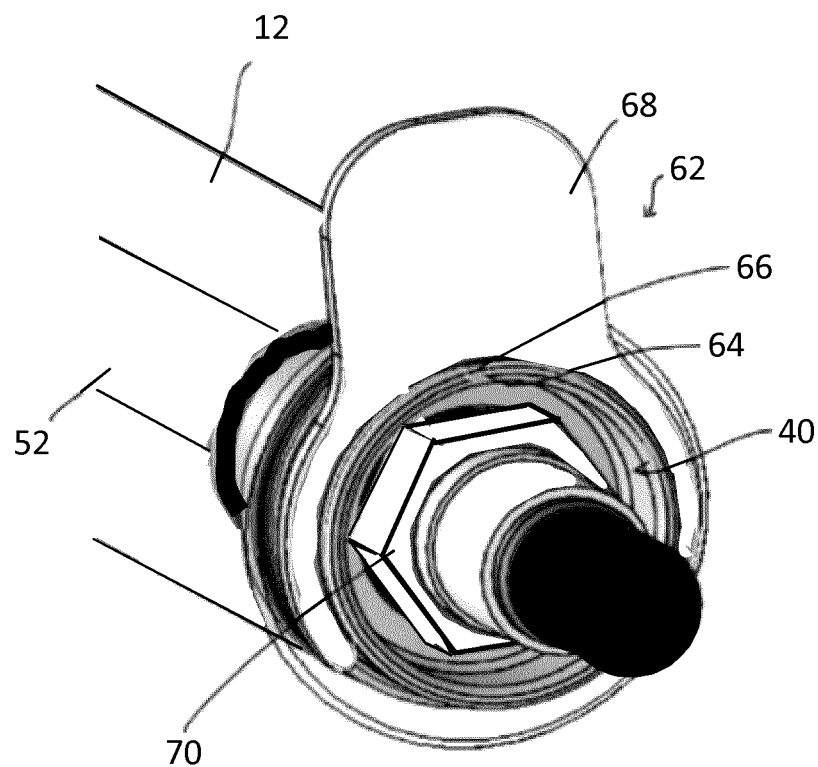
FIG. 13 is an enlarged, perspective view of a locking mechanism of the probe assembly of FIG. 1, shown in locked position.
Figure 14:
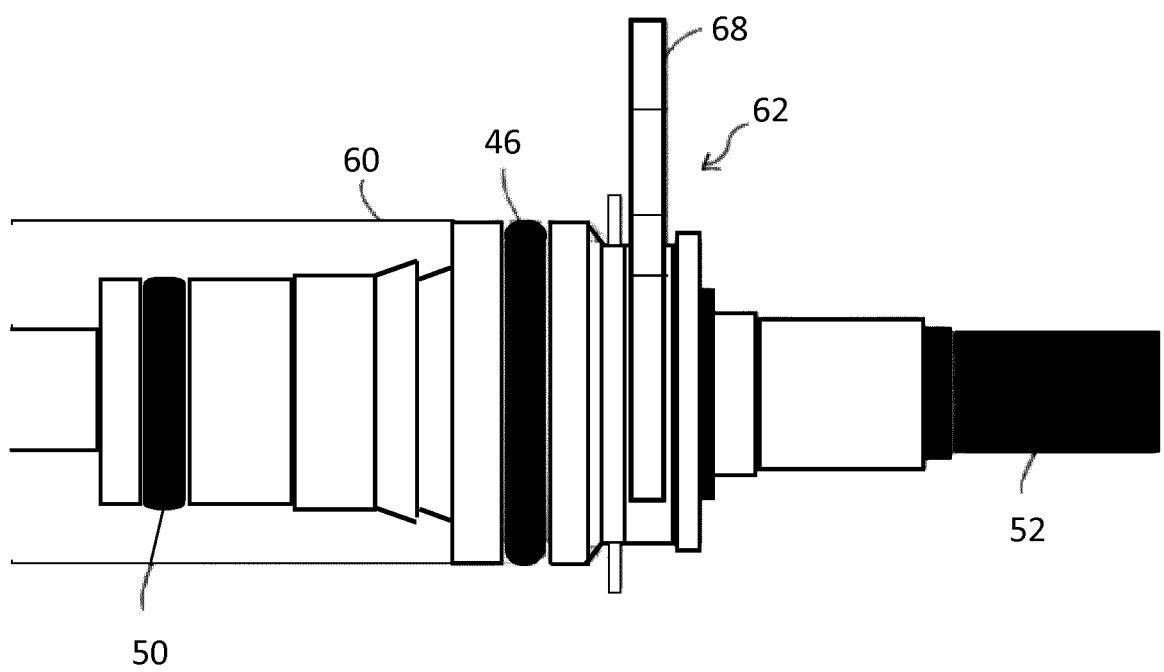
FIG. 14 is an enlarged, side elevational view of the locking mechanism of FIG. 13.
Figure 15:
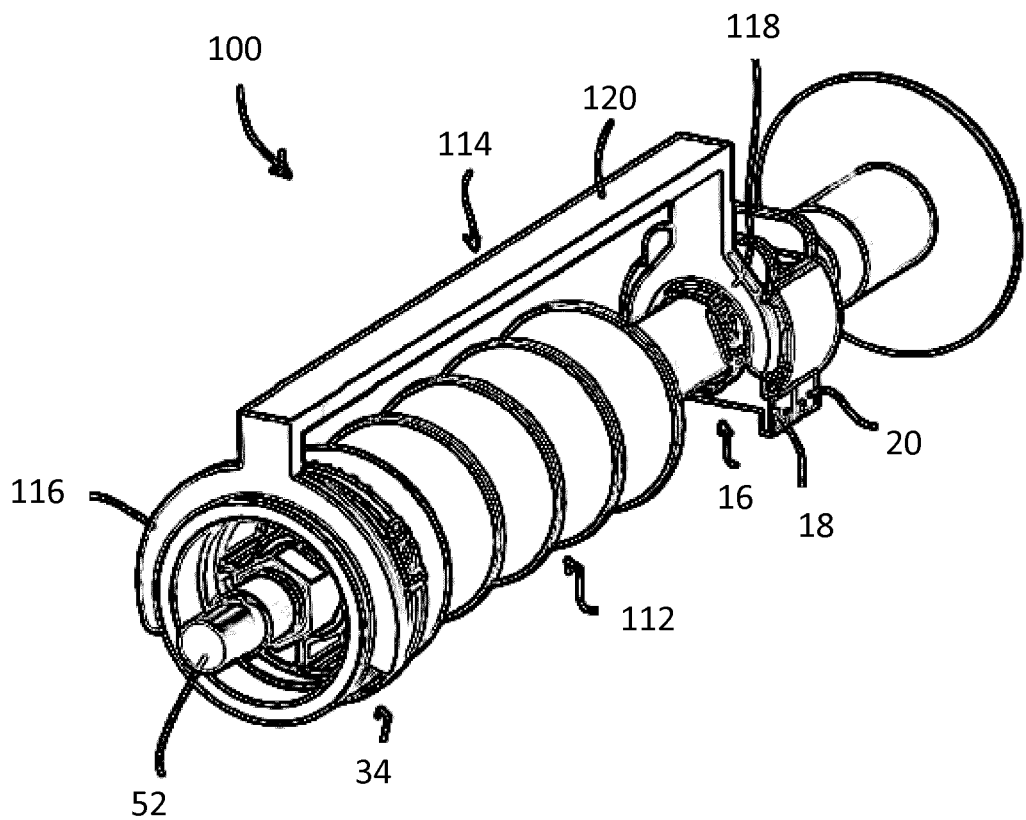
FIG. 15 is a rear, perspective view of a probe assembly, showing a locking key thereof, according to another embodiment of the invention.
Figure 16:
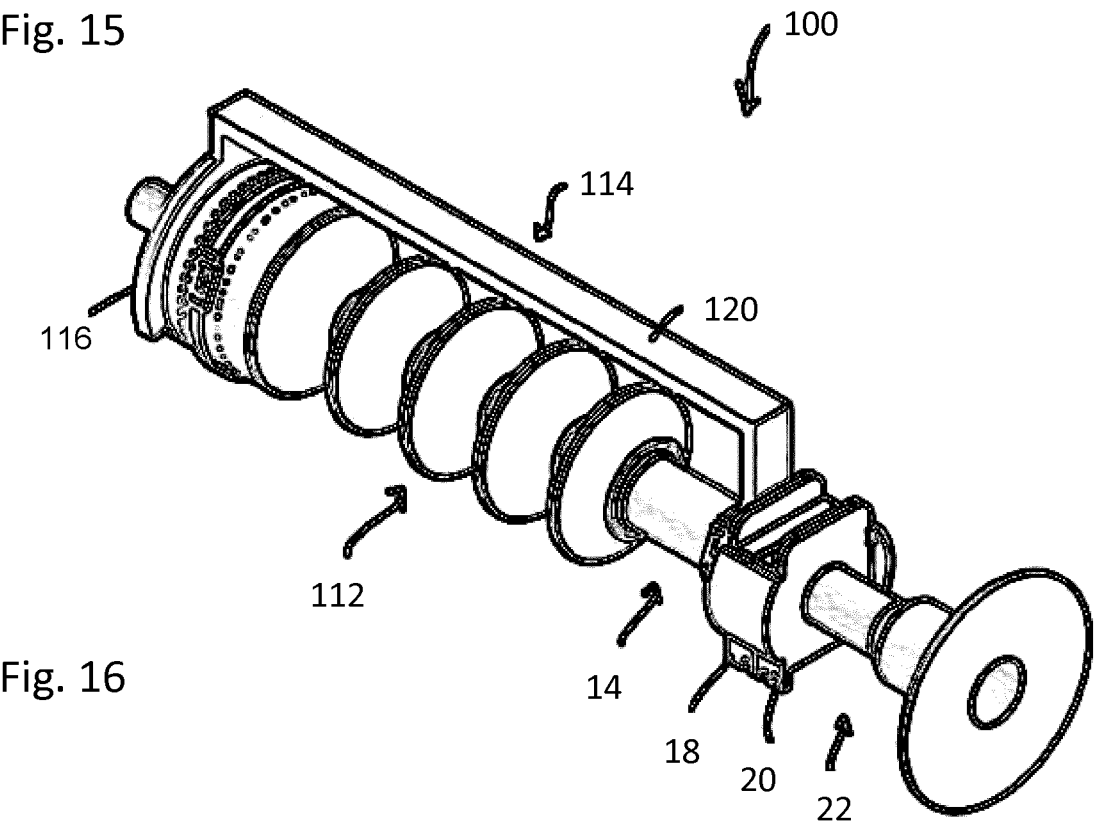
FIG. 16 is a front, perspective view of the probe assembly of FIG. 15.
Figure 17:
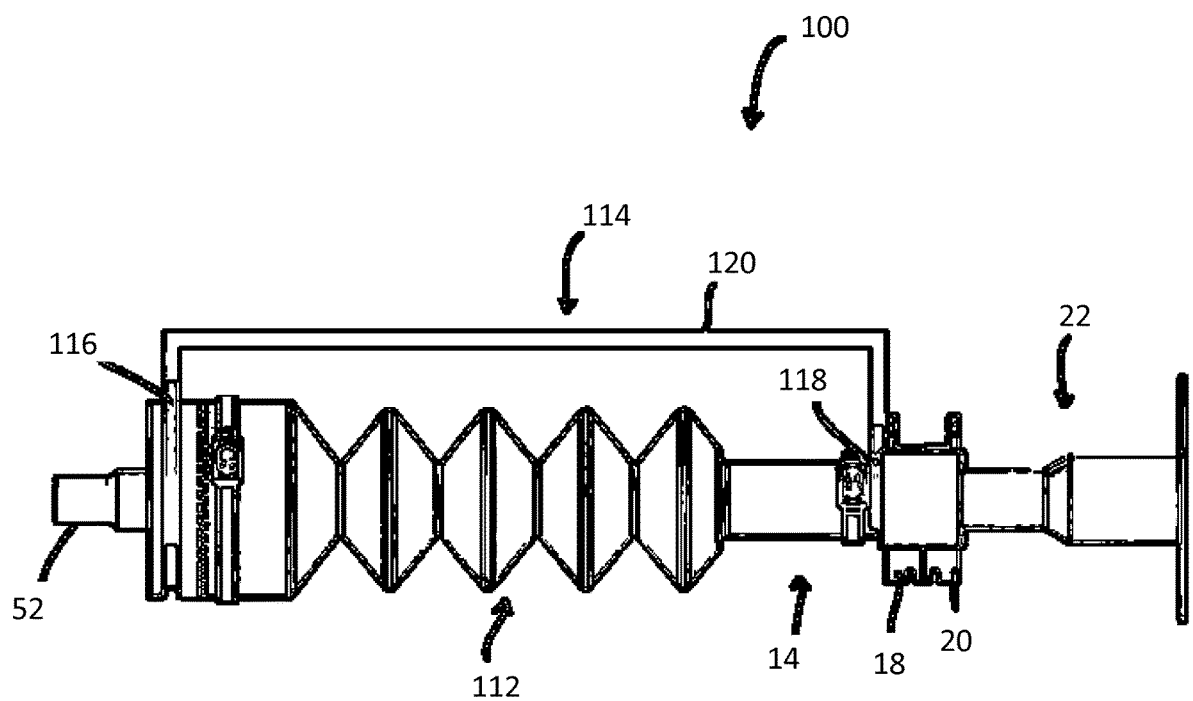
FIG. 17 is a side elevational view of the probe assembly of FIG. 15.
Figure 18:
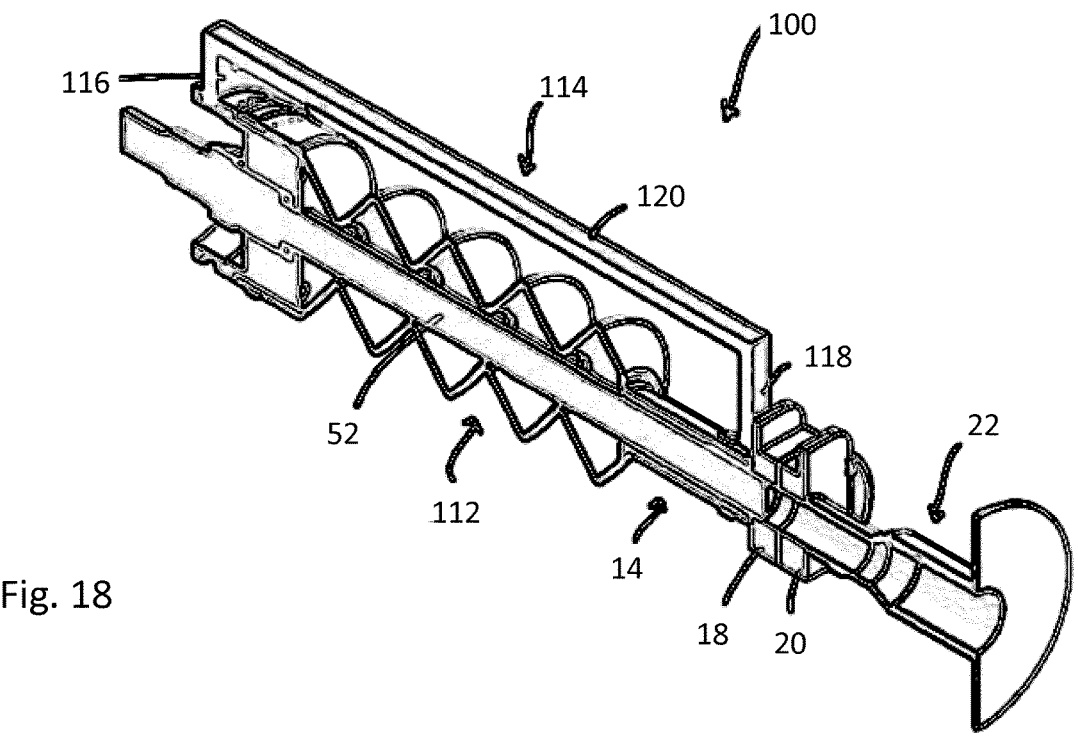
FIG. 18 is a cross-sectional perspective view of the probe assembly of FIG. 15.
Figure 19:
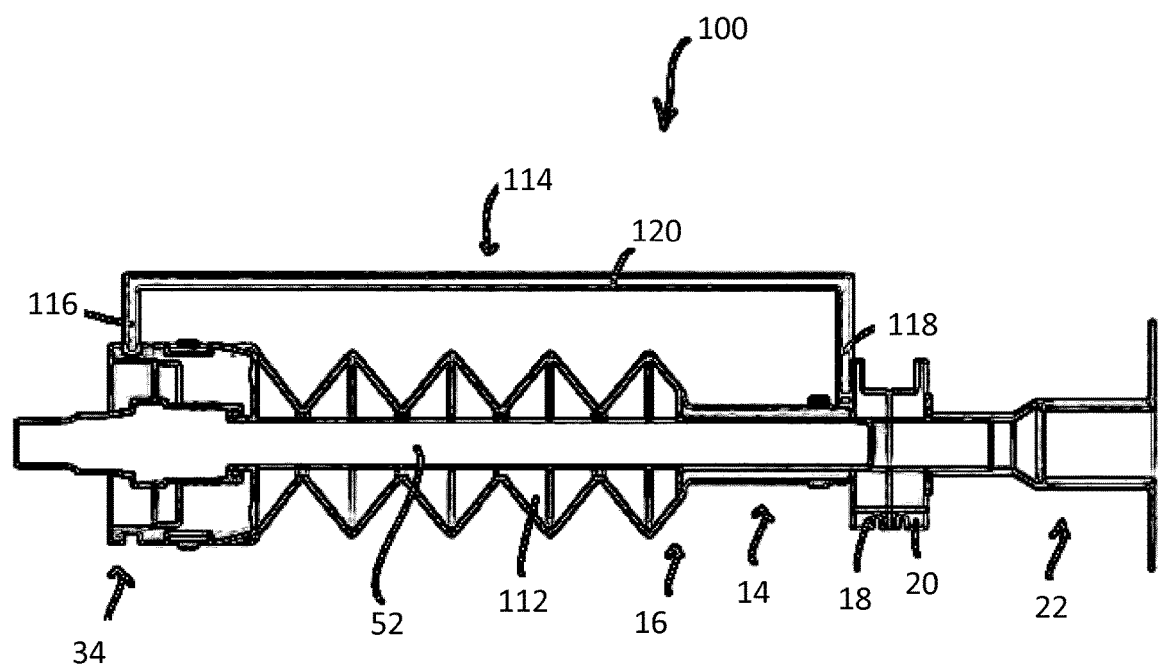
FIG. 19 is a cross-sectional side view of the probe assembly of FIG. 15.

The probe assembly, at its second end 34, further includes a locking mechanism in the form of a retaining clip 62 that prevents inadvertent axial movement of the plunger 40 and probe 52. In an embodiment, a slot or aperture is 64 formed in the peripheral wall of the plunger 40 and is configured to receive a detent 66 of the retaining clip 62, as best shown in FIGS. 4 and 13. As shown therein, the retaining clip 62 may be generally C-shaped and include a gripping tab 68. The retaining clip 62 may be placed over the proximal end of the plunger 40 (which extends slightly from the probe sheath 12 to expose the aperture 64) so that the detent 66 is received in the aperture 64. In this position, the retaining clip prevents the plunger 40 and probe 52 from being moved axially within the sheath 12. That is, only after the retaining clip 62 is removed by pulling on tab 68 can the plunger 40 and probe 52 move axially within the sheath 12.

Figure 7:
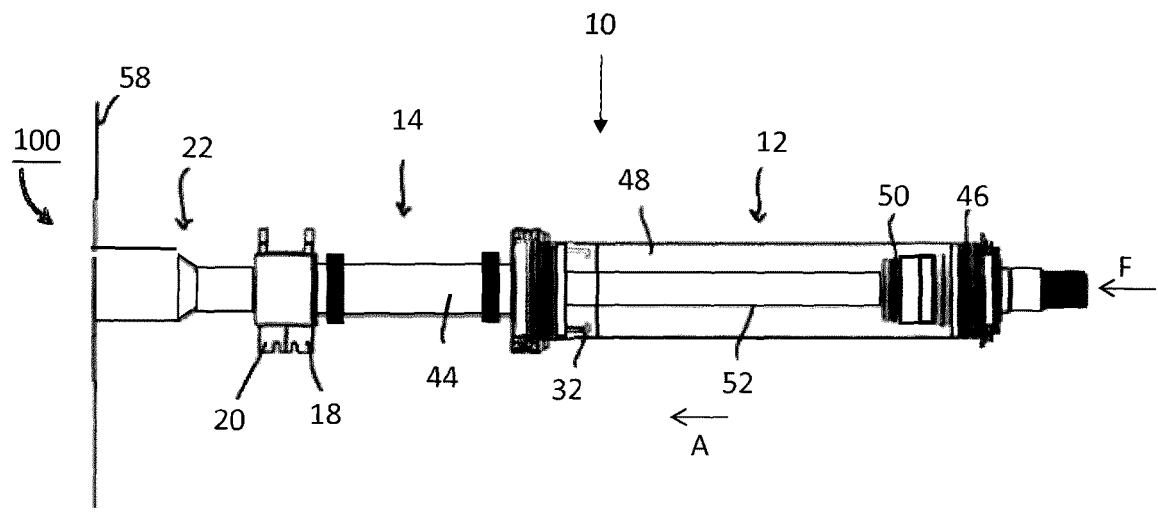
FIG. 7 is a side elevational view of the probe assembly of FIG. 1, wherein the probe assembly is joined to the bag or tubing and the probe is in secured position.

The probe sheath plunger 40 is positioned inside the opening 36 of the probe sheath 12 such that the sensor/probe body 52 with the sensing element can pass through the inside of the probe sheath 12 and extend into the tube 44 of the connector assembly 14. The probe sheath plunger 40 can be moved relative to the probe sheath 12 so that when the sensor or probe 52 needs to be inserted through a port on wall 58 of a flexible or semi-rigid container, column, or tubing, the plunger 40 is moved such that it decreases the internal volume 48 inside the probe sheath 12, and the sensor or probe 52 then moves down the sheath 12 to the connector assembly 14. Arrow, A, in FIG. 7 shows the direction of movement of the elongate probe body 52 longitudinally in the direction of the bag 100 during insertion of the probe 52.

With specific reference to FIGS. 7-10, the bag 100 can be outfitted with a connector (such as connector 22) such as by welding the connector to the inside of the bag wall. Like connector assembly 14, connector 22 may be an aseptic, sterile or sterilizable connector. The connector 22, as discussed above, incudes a mating portion 20 that allows for an aseptic or sterile connection to be made with mating portion 18 of connector assembly 14. In particular, the connector can include two separate portions, or parts 18, 20. These portions can mate together in a traditional male and female relationship, although other types of connectors may be used with the disclosed probe assembly. For example, the connector portions can connect to one-another in a non-mating fashion, such that each portion of the connector is identical. Clamping mechanisms can be utilized to ensure proper sealing and non-leaking function of the connector. The connector can include a non-permeable or semi-permeable membrane sealing the connectors portions from contamination from the ambient environment, this membrane being designed to be removed prior to insertion of the probe body through the connector. In an embodiment, a semi-permeable membrane is utilized to permit autoclaving of the interior of the probe sheath and any components or structures therein. The connector can be appropriately sized to match the diameter of a desired probe, vessel port, probe assembly connection size, or any other desired sizing variable. The type of connector can be selected without regard to the embodiment of the probe sheath type, and may be an aseptic connector or sterilize (or sterilizable) connector. Aseptic connectors are available from various commercial sources, such as Colder Products, Pall, Millipore and GE Healthcare.

The probe sheath plunger 40 can be disposed within the probe sheath 12 such that no ambient air, liquids, or other matter from the exterior of sheath 12 can pass to the sheath interior 48. The probe sheath plunger 34 can be formed of a rubber material such that the plunger can slide along the probe sheath 12 and such that the plunger 40 forms a seal directly against the probe sheath 12. In other embodiments, as explained above, the assembly can include seals. In yet another embodiment there is no plunger 40; instead, for example, a portion of the probe body serves as the actuator. In this case, the seal 46 contacts the elongate probe body directly, aseptically sealing the interior 48 from the ambient environment.

With further reference to FIGS. 5-8, in use, connector assembly 14 is first coupled to the distal end 16 of the probe sheath 12. Retaining clip 62 is engaged with the plunger 40 at the second end 34 of the probe sheath 12 to prevent constrain axial movement of the plunger 40. Probe 52 is then inserted into the second end 34 of the probe sheath 12, through the opening 42 in the plunger 40. The probe 52 is then rotated (such as through a socket or other tool that engages a hex head 70 of the probe 52) to threadedly couple the probe 52 to the plunger 40 and establish a seal between the probe 52 and plunger 40, via a sealing element on the probe or probe plunger, to isolate the environment inside the sheath 12 from the ambient environment. The entire probe assembly, including any sheaths, connectors, and tubes, as well as the probe itself, may then be sterilized prior to inserting the probe into the reactor vessel. Common methods of sterilization include, but are not limited to, autoclaving, radiation treatment, and chemical treatment. When an autoclave is used, it can be important for steam to reach all of the interior surfaces of a probe assembly, as well as the exterior portions.

Once the probe 52 is inserted into the sheath 12 and coupled to the plunger 40, the probe 52 is prevented from moving axially relative to the sheath 12 by the retaining clip 62. This eliminates the possibility of the distal end of the probe 52 puncturing the sterile barrier/membrane (not shown) in place on the distal end of the connector assembly 14, ensuring that a sterile environment is maintained within the sheath 12 and around the probe 52. In addition, the retaining clip 62 prevents the plunger 40 from moving back and forth within the sheath 12, which could also compromise sterility at the second end 34.

Figure 8:
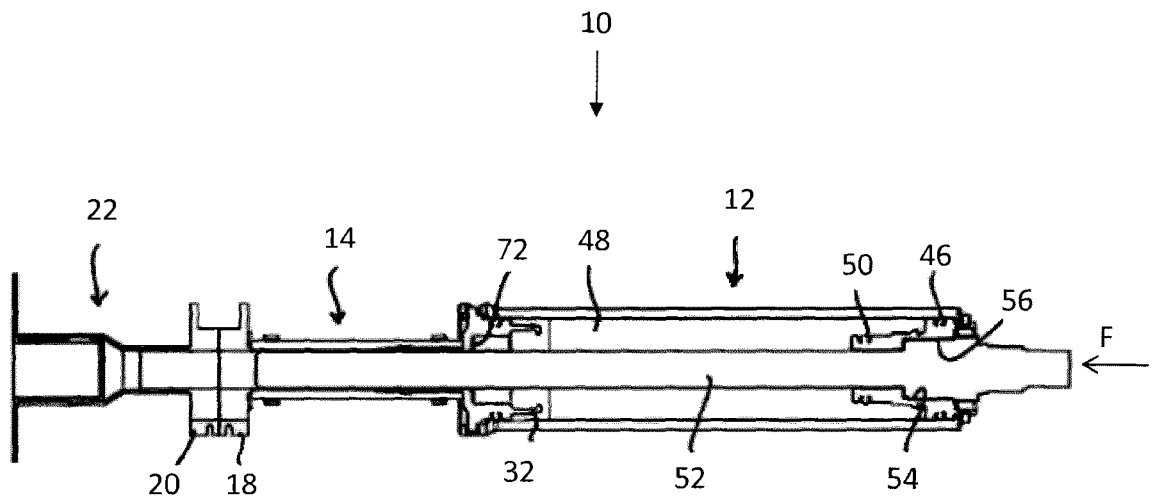
FIG. 8 is a cross-sectional side view of the probe assembly of FIG. 1, wherein the probe assembly is joined to the bag or tubing and the probe is in secured position.
Figure 9:
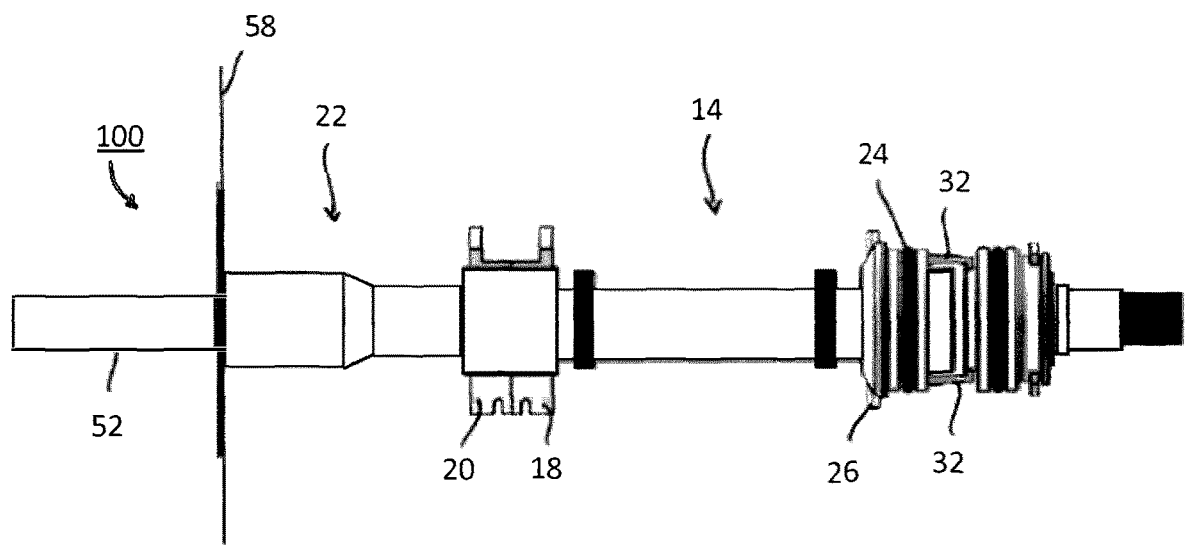
FIG. 9 is an enlarged, side elevational view of a distal portion of the probe assembly of FIG. 1, showing the probe in deployed position.
Figure 10:
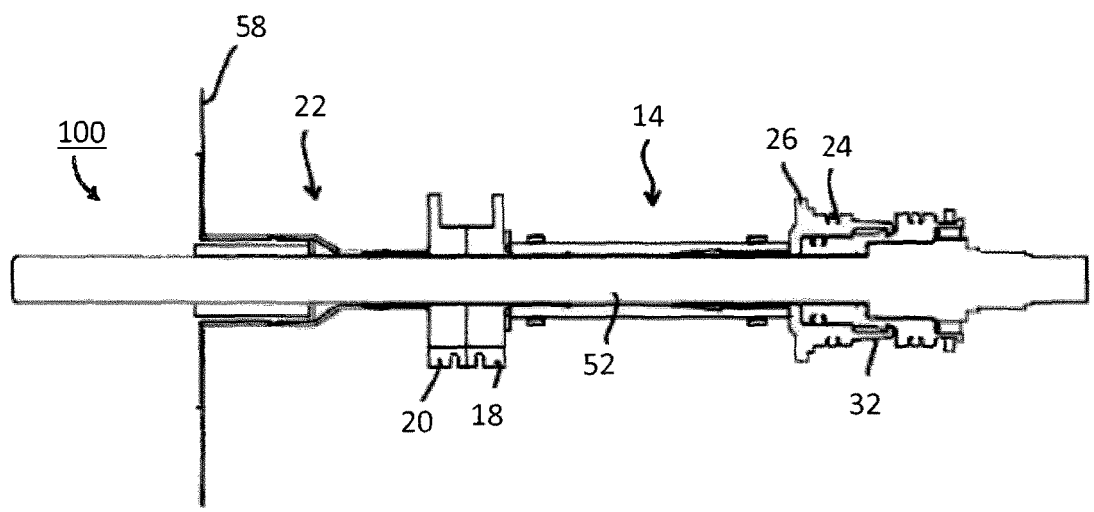
FIG. 10 is an enlarged, cross-sectional side view of a distal portion of the probe assembly of FIG. 1, showing the probe in deployed position.

When it is desired to inset the probe 52 into a vessel, bag or tube, the connector mating portion 18 on the probe assembly 10 is engaged with the connector mating portion 20 that is attached to the bag 100 to form an aseptic connection therebetween, as shown in FIGS. 7 and 8. The membranes in place on the respective mating portions 18, 20 can then be removed, thereby establishing fluid communication between the probe assembly 10 and the bag 100. In this position, the plunger 40 and probe 52 are still prevented from movement with respect to the sheath 12, as they are held in fixed position by the retaining clip 62. Once the retaining clip 62 is removed, however, by pulling on tab 68, an axial force, F, may be applied to the probe 52 and/or plunger 40 from the second end 34 to plunge the probe 52 into connector 22 and into the bag 100, as shown in FIGS. 9 and 10.

Figure 11:
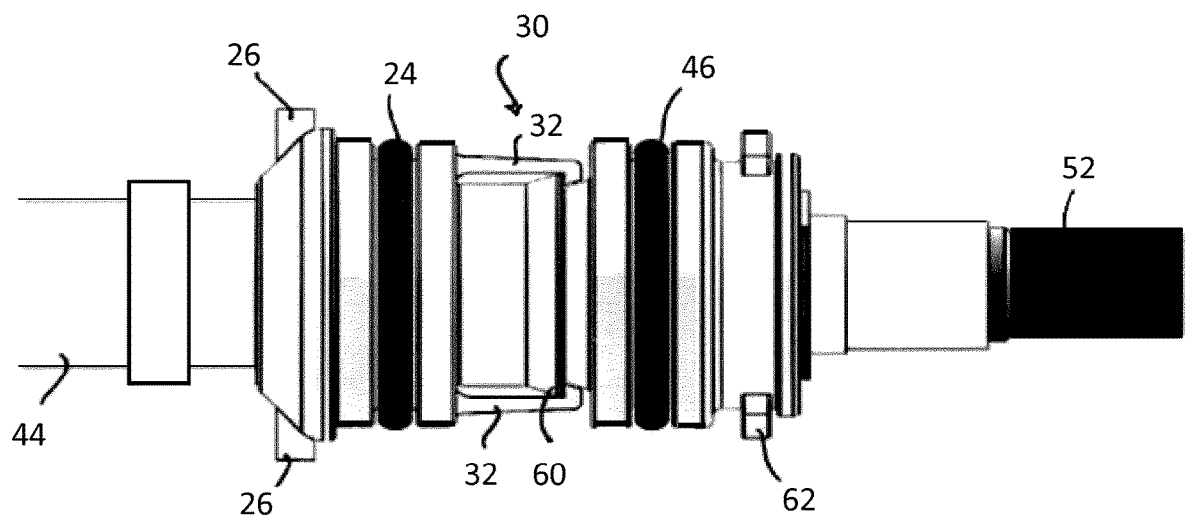
FIG. 11 is an enlarged, side elevational view of a latch mechanism of the probe assembly of FIG. 1, shown in latched position.
Figure 12:
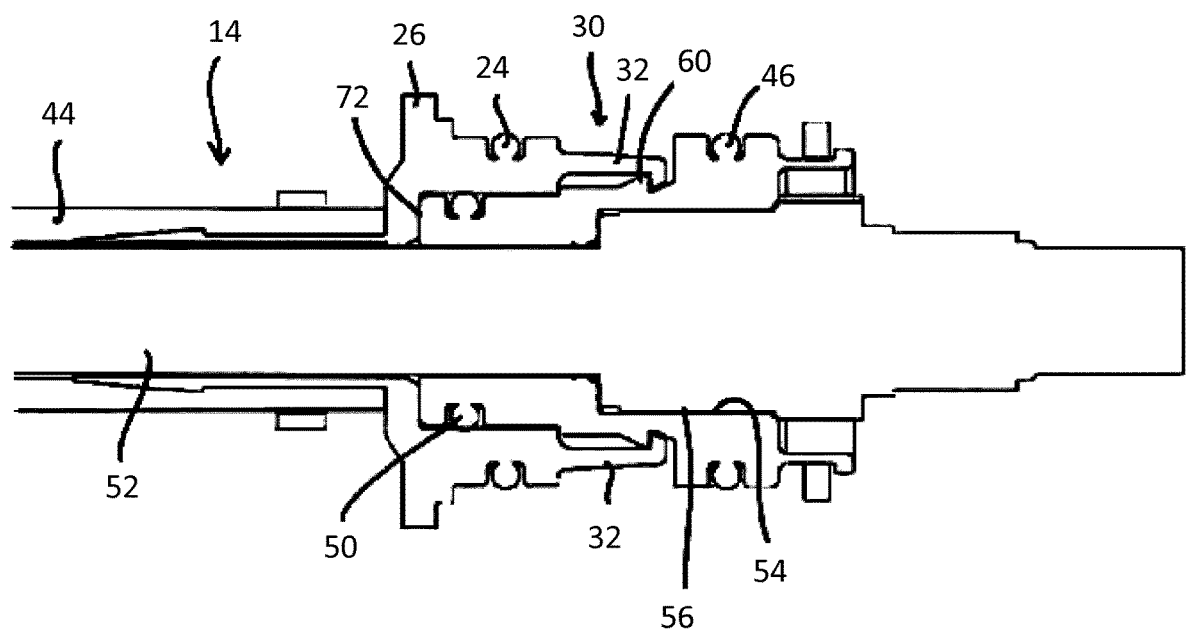
FIG. 12 is an enlarged, cross-sectional side view of the latch mechanism of FIG. 11.

As the probe 52 is urged towards the distal end 16 of the probe sheath 12 into the bag 100, the plunger 40 will contact the proximal end of the connector assembly 14, which includes a surface that functions as a position stop 72 that limits further forward travel of the plunger 40 and probe 52 (in embodiments, the position stop 72 may be considered part of the latch mechanism 30). In other embodiments, the structure that limits forward movement of the plunger 40 may be threads, a friction fit, a bayonet connector, a clamp device, or a pin connection, although other mechanisms performing this function may also be utilized without departing from the broader aspects of the invention. During this action, the resilient arms 32 of the latch mechanism 30 snap over the flange 60 one the plunger 40, as best shown in FIGS. 11 and 12. This action results in an audible and/or tactile indication that the probe 52 has been urged forward to the extent possible and is in proper position within the bag 100. In particular, in addition to serving as a position stop limiting further forward travel of the probe, the latch mechanism 52 also notifies a user when the predetermined probe insertion depth has been achieved. Moreover, the latch mechanism 30 also prevents the probe 52 from inadvertently being moved backwards within the sheath 12, ensuring that the desired insertion depth (namely, the distance of the distal end of the probe beyond the probe sheath or connector assembly) is maintained throughout the cell cultivating or other process. In an embodiment, the sheath 12 and connector assembly 14 are sized and dimensioned so that when fully deployed, the probe 52 protrudes approximately ¼" into the bag 100. After use, the probe 52 may be unthreaded from the plunger 40 and removed from the sheath for reuse. This reuseability is further facilitated by the removable attachment of the connector assembly 14 with the sheath 12.

The probe assembly 10 of the invention therefore provides for a consistent, reliable and repeatable probe insertion depth, ensuring that precise measurements of batch parameters are obtained. This functionality is provided by the combination of the rigid sheath and connector assembly (and the fixed longitudinal dimension thereof relative to the length of the probe), and the latch mechanism 30. Such functionality has heretofore typically not been possible, as existing probe assemblies have allowed for longitudinal movement of the probe even after deployment. In addition, the locking mechanism in the form of a retaining clip 62 ensures that inadvertent probe movement prior to deployment is prevented, thereby eliminating the possibility of puncturing the sterile membrane/barrier with the tip of the probe prior to deployment, which can potentially compromise sterility. With existing probe assemblies, however, the probe and plunger have not been restrained, but rather have been free to move at all times with respect to the sheath, rendering such assemblies prone to inadvertent puncture or damage to the sterile barrier on the end of the connector. The probe assembly of the invention remedies these deficiencies and therefore provides a more user-friendly device that can be reused in a repeatable manner.

While the latch mechanism 30 has been described herein as being a pair of resilient arms that engage a flange on the plunger, the latch mechanism may take the form of any mechanical structure that limits axial movement of the probe with respect to the sheath. For example, the latch mechanism may be constructed as a bayonet-type connector, screw threads or pure interference of the probe or plunger with a limit stop on the sheath or connector assembly. Moreover, while the locking mechanism has been described herein as taking the form of a retaining clip having a detent that is received in a slot in the plunger, any mechanical means of preventing translation of the probe may be utilized to solve the issue of accidental probe translation (such as a spacing device or rigid linkage for existing bellows-type probe sheaths). In particular, where a flexible, bellows-type sheath is utilized, the probe assembly may include a rigid linkage preventing axial movement of the probe into the bag until the linkage is removed or disabled.

The sensor used in a probe sheath 12 according to an embodiment of the invention can be any type of sensor. Non-limiting examples include conductivity, pH, dissolved oxygen, turbidity and temperature sensors. The probe assembly 10 according to an embodiment of the present invention facilitates the removal or retraction of a sensor from a flexible or semi-rigid container or a flexible or semi-rigid tubing so that the sensor can be sterilized and re-used in another device.

While the invention has been described herein as utilizing a rigid or substantially rigid probe sheath that allows for the locking and latching mechanisms described above to restrain longitudinal movements of the plunger and probe to prevent inadvertent movement of the probe prior to deployment and to ensure a consistent and repeatable probe insertion depth, it is contemplated that the same benefits may also be achieved for accordion or bellows-type probe sheaths. For example, with reference to FIGS. 15-19, an embodiment, a probe assembly 100 according to another embodiment of the invention is illustrated. The probe assembly 100 is substantially similar to the probe assembly described above in connection with FIGS. 1-14, however, rather than having a rigid sheath 12, the assembly 100 has an accordion or bellows-type, flexible sheath 112 that will fold onto or into itself in response to a compressive force. As is known in the art, the probe 52 is fixedly coupled to the proximal end 34 of the probe sheath 112 (rather than to a sliding plunger) and is deployed into a vessel or tubing by urging the probe towards the distal end 16 of the sheath 112. This force causes the flexible sheath 112 to fold in an accordion-like manner, permitting the distal end of the probe to extend through the connector 22 and into the vessel or tubing attached thereto.

As shown in FIGS. 15-19, in an embodiment, the probe assembly 100 also includes a locking key or linkage 114. The locking key 114 is substantially U-shaped and includes opposed gripping arms 116, 118 and a rigid linking member 120 extending substantially orthogonal from, and connecting, the opposed gripping arms 116, 118. In an embodiment, the linking member has a length that generally corresponds to the combined length of the sheath 112, in its extended position, plus connector 14, such that the arms 116, 118 are positioned so as to engage rigid structures at the proximal end 34 and distal end 16 of the sheath, respectively. In an embodiment, the length of the linking member 120 is such that it positions the gripping arms 116, 118 to engage any non-collapsible structure of the probe assembly 100 on the opposed proximal and distal ends 34, 16 thereof (that is, any structure other than the collapsible bellows portion). The arms gripping arms 116, 118 may, for example, take the form of resilient C-clips each having an inner diameter that closely corresponds to the diameter of generally cylindrical structures at the proximal end 34 and distal end 16 of the sheath (or connector 14). In an embodiment, the distal gripping arm 118 may be positioned just rearward of, and abut, mating connector portion 18 of connector assembly 14.

In operation, when the probe 52 is inserted into the sheath 112 and the probe assembly 100 is connected to a connector (e.g., connector 22) attached to a vessel or tubing, the locking key 114 maintains the sheath 112 from collapsing when an axial force is exerted on the sheath 112 or probe 52. In particular, the rigid linking member 120 resists any such axial force, preventing collapsing of the bellows and thereby preventing longitudinal translation of the probe 52 beyond the connector 14 and into the bag or vessel. When it is desired to deploy the probe 52, the locking key 114 may simply be removed from the assembly 100, allowing the bellows to collapse in response to an axial force and allowing the distal end of the probe 52 to advance beyond the connector 14 and into the vessel or tubing.

Figure 20:
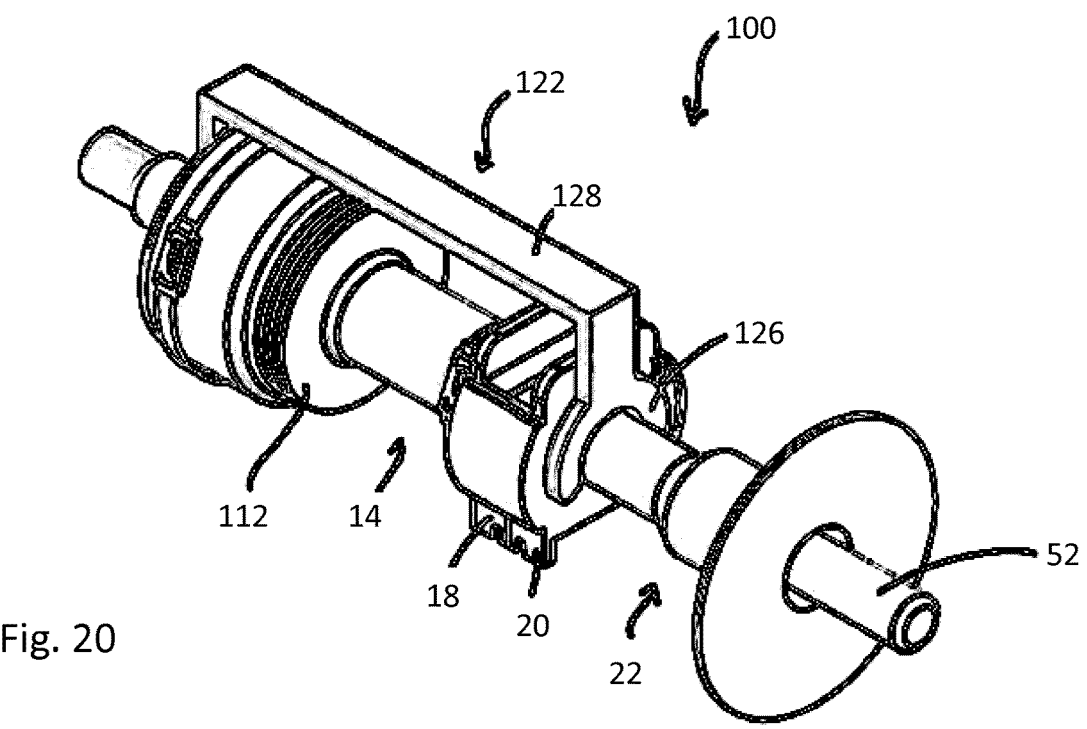
FIG. 20 is a front, perspective view of the probe assembly of FIG. 15, showing a restraining key thereof, according to an embodiment of the invention.
Figure 21:
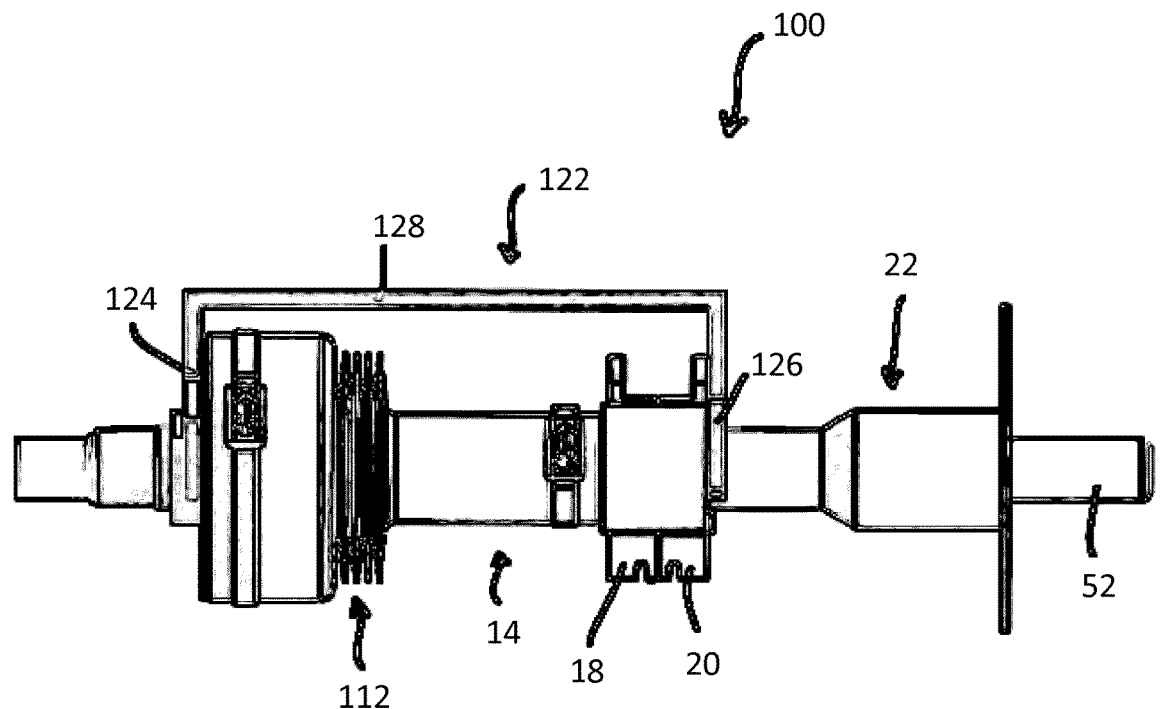
FIG. 21 is a side elevational view of the probe assembly of FIG. 20, showing the restraining key.
Figure 22:
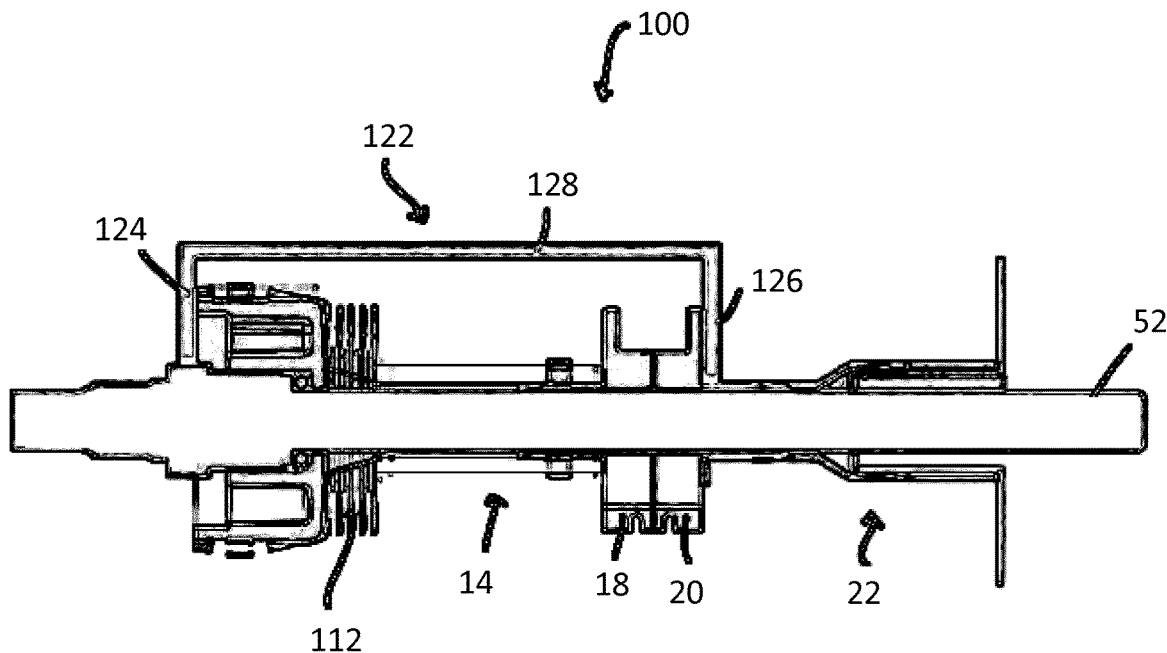
FIG. 22 is a cross-sectional side view of the probe assembly of FIG. 20, showing the restraining key.
Figure 23:
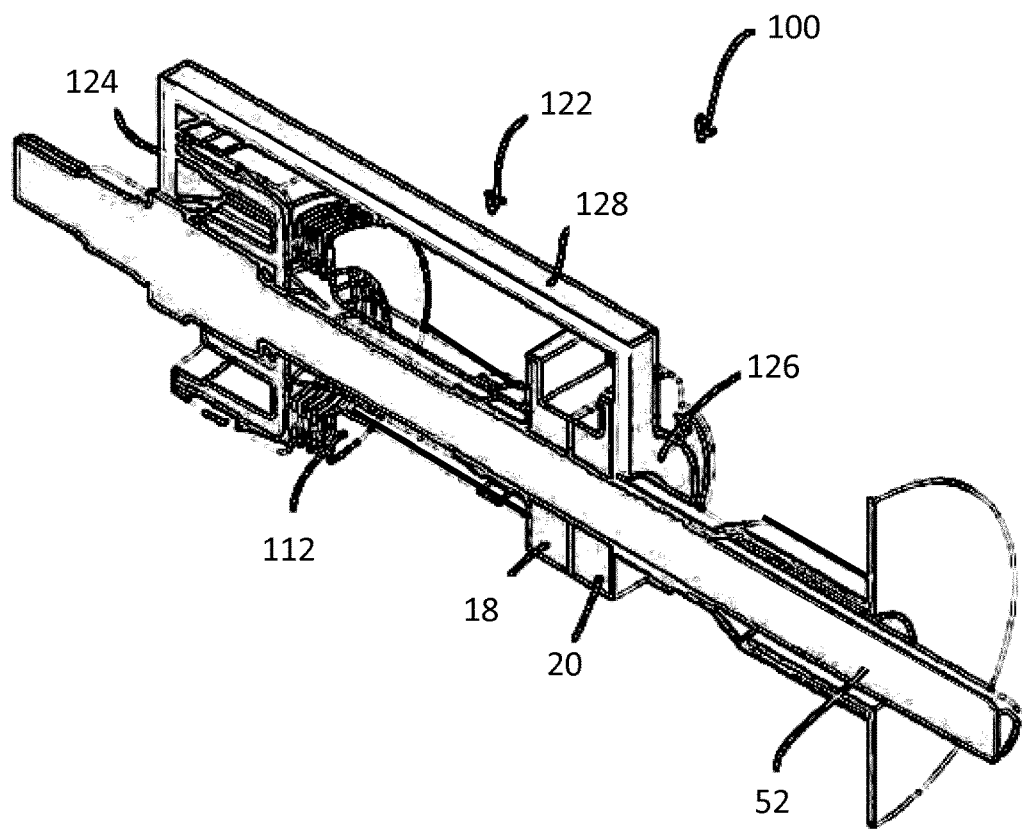
FIG. 23 is a cross-sectional perspective view of the probe assembly of FIG. 20, showing the restraining key.
Figure 24:
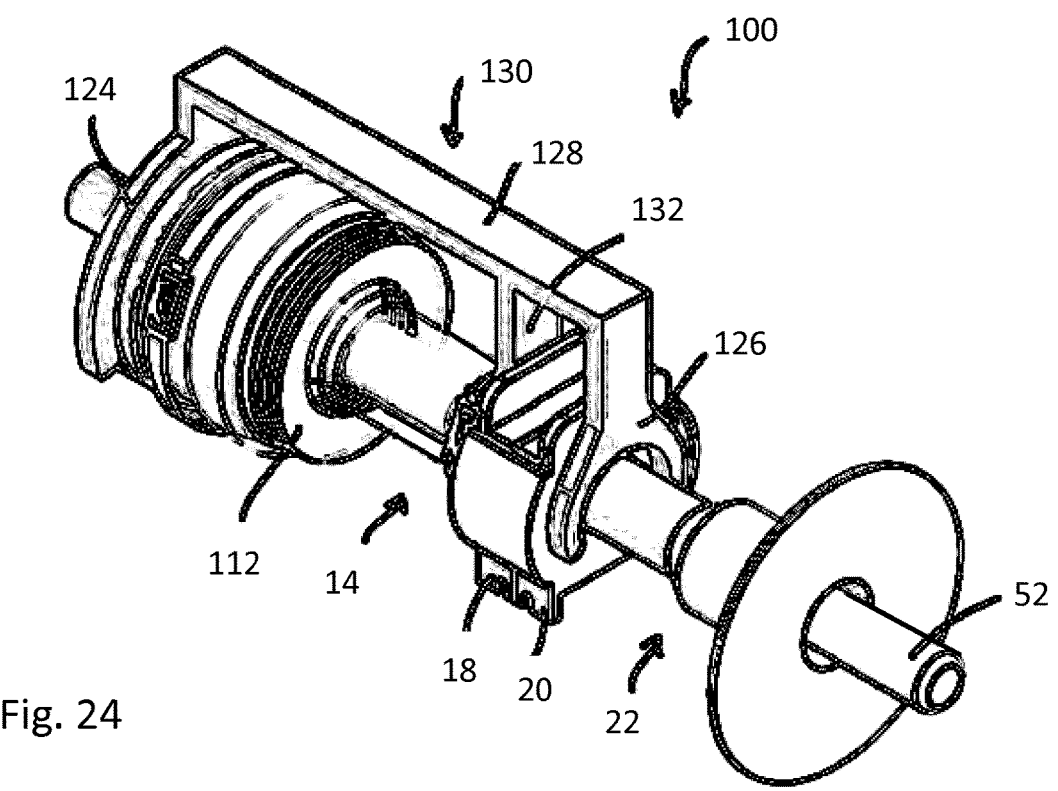
FIG. 24 is a front, perspective view of the probe assembly of FIG. 15, showing a restraining key thereof, according to another embodiment of the invention.
Figure 25:
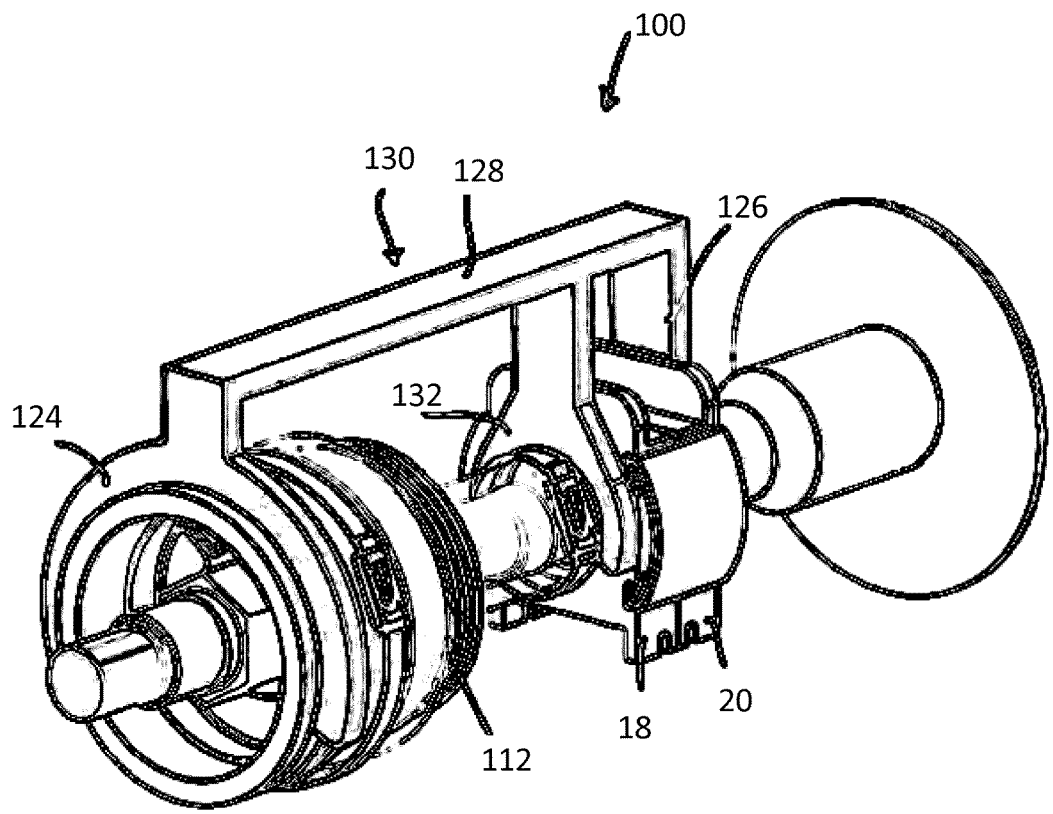
FIG. 25 is a rear, perspective view of the probe assembly of FIG. 24, showing the restraining key.

Referring now to FIGS. 20-23, in an embodiment, the probe assembly 100 may also include a restraining key 122. The restraining key 122 has a configuration similar to that of locking key 114. In particular, the key 122 is substantially U-shaped and includes opposed gripping arms 124, 126 and a rigid linking member 128 extending substantially orthogonal from, and connecting, the opposed gripping arms 124, 126. In an embodiment, the rigid linking member 128 has a length that allows the gripping arm 124 to engage a rigid or semi-rigid structure of the probe assembly 100 at the proximal end 34, and gripping arm 126 to be positioned just beyond mating connector portion 20 of connector 22, when the bellows is in the collapsed position. The length of the rigid linking member 128 may be selected to define a minimum insertion depth of the probe. As shown in FIGS. 20-23, the restraining key 122, prevents rearward longitudinal movement of the probe and resists any axial force in the rearward direction. In particular, when the restraining key 122 is in position, withdrawal of the probe 52 from its deployed position cannot be effected due to the interface of the arm member 126 with the distal surface of the connector mating portion 20, as illustrated in FIG. 20. Accordingly, the function of the restraining key 122 is similar to the resilient arms of the latching mechanism discussed above in connection with FIGS. 1-14. In an embodiment, both the locking key 114 and restraining key 122 are removable from the assembly 100 so that the probe 52 can be locking in position prior to deployment and retained in position subsequent to deployment (to prevent withdrawal of the probe 52).

Figure 26:
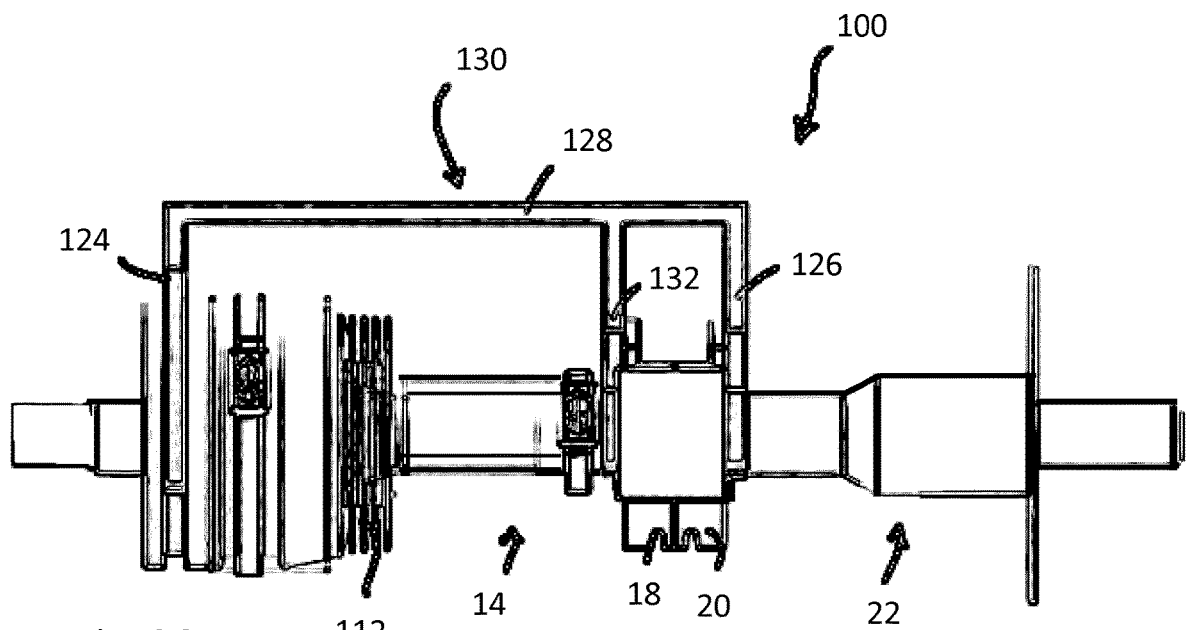
FIG. 26 is a side elevational view of the probe assembly of FIG. 24, showing the restraining key.
Figure 27:
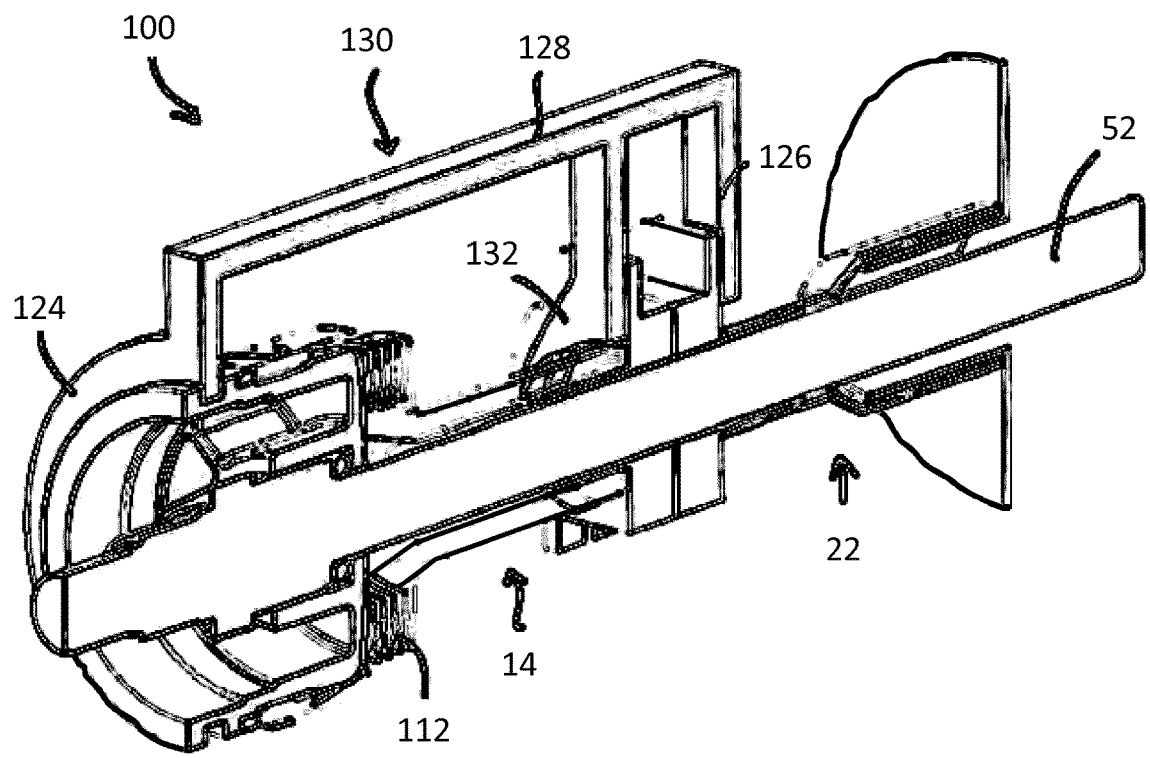
FIG. 27 is a cross-sectional perspective view of the probe assembly of FIG. 24, showing the restraining key.
Figure 28:
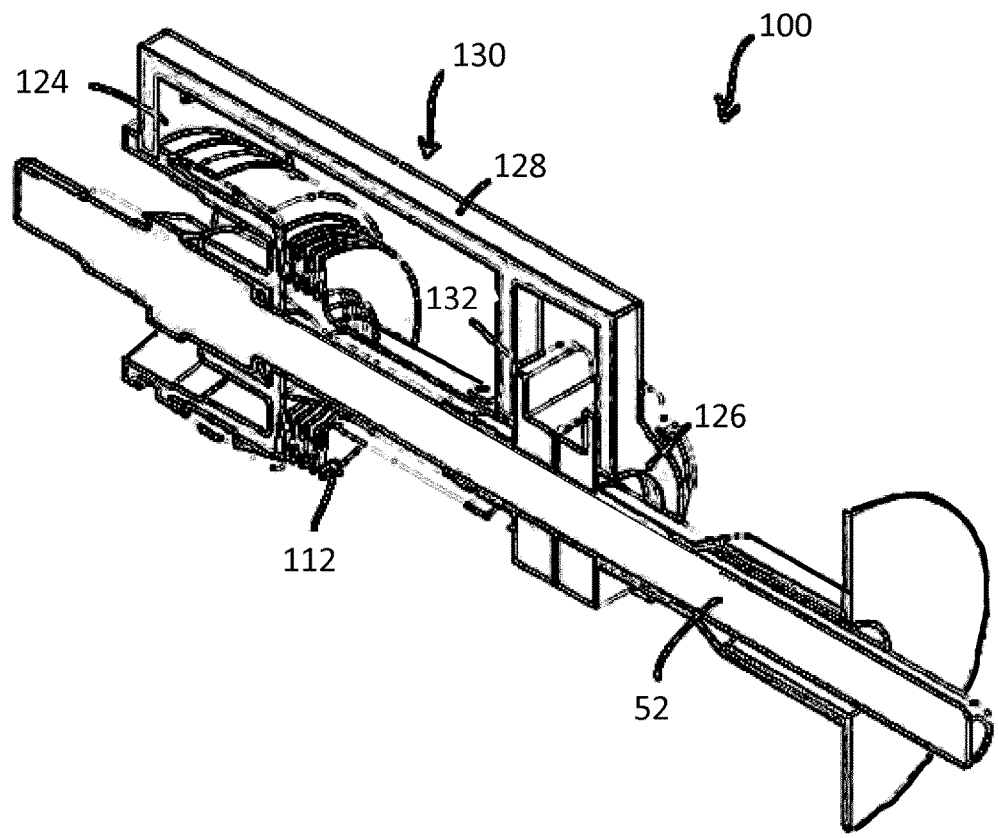
FIG. 28 is another cross-sectional perspective view of the probe assembly of FIG. 24, showing the restraining key.
Figure 29:
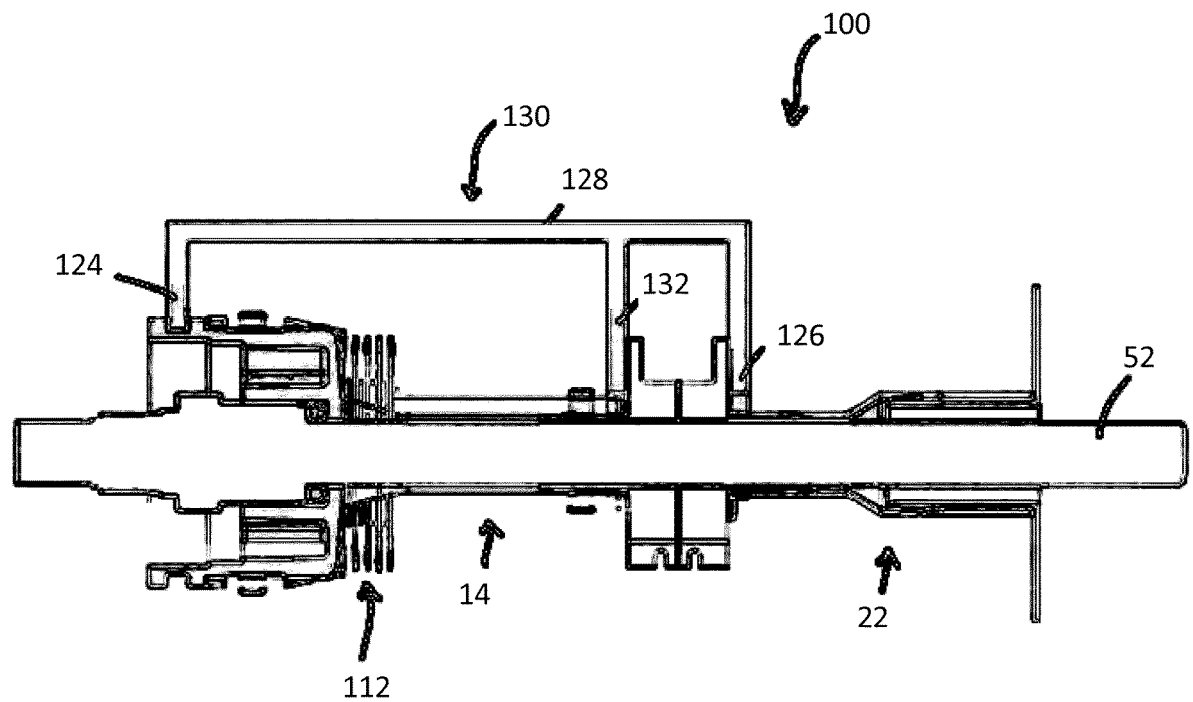
FIG. 29 is a cross-sectional side view of the probe assembly of FIG. 24, showing the restraining key.

Referring now to FIG. 24-29, another possible configuration for the restraining key is illustrated. As shown therein, restraining key 130 is similar to restraining key 114, however, in addition to gripping arms 124, 126, the restraining key 130 also has an intermediate gripping arm 132 that is configured to engage the connector assembly 14 at a point just rearward of the mating connector portion 18. Accordingly, as best shown in FIG. 26, the gripping arms 126, 132 are configured to engage the probe assembly 100 on opposite sides of the respective connector mating portions 18, 20. In operation, once the probe 52 is deployed into a vessel or tubing by collapsing the sheath bellows 112 in the manner described above, the restraining key 130 may be attached to the assembly 100. When attached, the probe 52 is thereby prevented from moving either rearward or forward (by engagement/interference of gripping arm 126 with connector mating portion 20, and gripping arm 132 with connector mating portion 18), maintaining the position of the distal end of the probe 52 at a predetermined distance beyond the connector 22 and into the bag or tubing attached thereto. The restraining key 132 therefore provides a similar function to that of the resilient arms of the latching mechanism and the position stop described above in connection with FIGS. 1-14.

Figure 30:
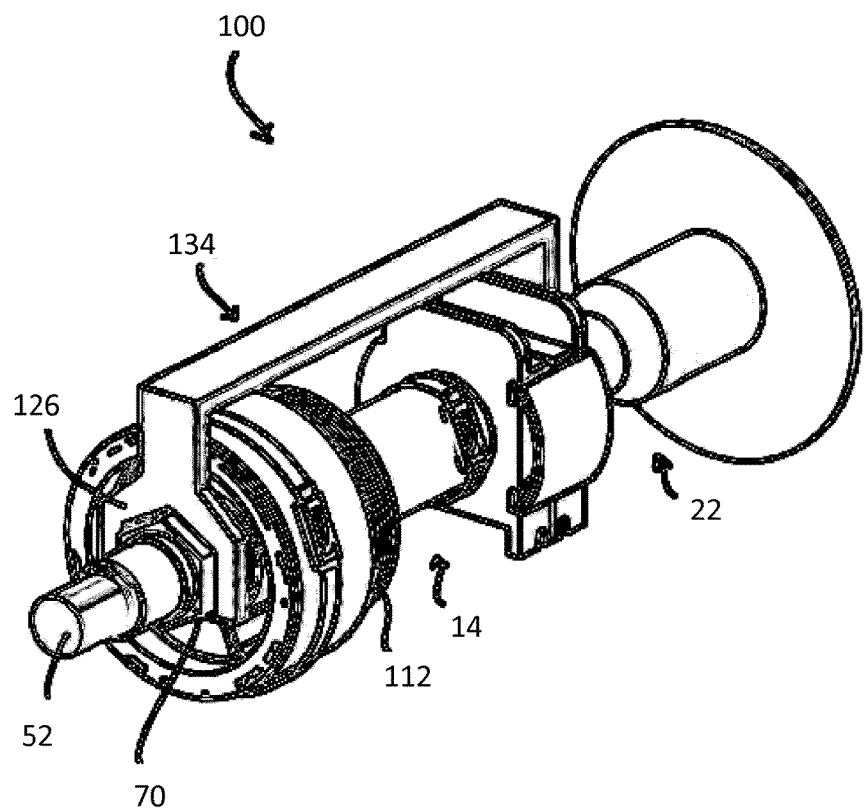
FIG. 30 is a rear perspective view of a probe assembly showing a restraining key according to another embodiment of the invention.

Finally, with reference to FIG. 30, it is shown that the gripping arm of either the locking key or restraining key may be configured to engage a portion of the probe 52 rather than the sheath 112. For example, in an embodiment, a restraining key 134 may have a proximal arm member 136 configured to engage the head (e.g., hex head 70) of the probe 52.

Embodiments of the invention therefore provide a means to prevent inadvertent deployment (indeed, any translational movement) of the probe, as well as a means to maintain the probe at a precise and repeatable insertion depth once deployed, for either rigid or flexible, bellows-type probe sheaths. In particular, the invention described herein, in any implementation, allows for a linear or substantially linear insertion and locking of the probe at a known or predetermined distance beyond the assembly (and/or into a vessel or tubing) without requiring deflection of the corresponding tube or connector assembly affixed to the vessel or tubing. This is in contrast to certain exiting assemblies which require deflection of the connector on the vessel to allow for angled insertion of the probe.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A probe assembly for inserting a probe into a vessel or tubing, the assembly comprising:
    a probe sheath having a proximal end and a distal end and being configured for operative coupling to a vessel or tubing, the probe sheath being configured to receive a probe and to permit movement of the probe towards the distal end of the probe sheath; and
    a connector assembly attached to the distal end of the probe sheath, the connector assembly allowing for coupling of the probe sheath to the vessel or tubing;
    a latch mechanism provided at a proximal end of the connector assembly; and
    a locking mechanism configured to restrain longitudinal movement of the probe with respect to the sheath in a locked state;
    wherein the locking mechanism may be unlocked to allow for movement of the probe with respect to the sheath.

2. The probe assembly of claim 1, wherein:
    the connector assembly is configured to couple to a mating connector associated with the vessel or tubing.

3. The probe assembly of claim 1, wherein:
    the probe sheath is substantially rigid and has a fixed length;
    wherein the probe assembly further includes a plunger slidably received within the probe sheath; and
    wherein the plunger is configured to sealingly engage the probe sheath and the probe.

4. The probe assembly of claim 3, wherein:
    the locking mechanism includes a clip having a detent that is configured to be received in a corresponding aperture in the plunger.

5. The probe assembly of claim 1,
    wherein the latch mechanism configured to restrain movement of the probe with respect to the probe sheath after deployment of the probe into the vessel or tubing and to maintain a distal end of the probe a predetermined distance beyond the probe sheath.

6. The probe assembly of claim 5, wherein:
    the latch mechanism provides an audible or tactile indication that the predetermined distance has been achieved.

7. The probe assembly of claim 5, wherein:
    the latch mechanism includes at least one resilient arm located at a distal end of the probe sheath and a flange formed on a peripheral surface of the plunger;
    wherein the at least one resilient arm is configured to engage the flange to restrain longitudinal movement of the plunger and probe towards the proximal end of the probe sheath.

8. The probe assembly of claim 5, wherein:
    the latch mechanism includes a structure that limits movement of the plunger toward the distal end of the probe sheath to provide the predetermined distance of the distal end of the probe beyond the probe sheath.

9. The probe assembly of claim 8, wherein:
    the structure is one of a position stop, threaded element or bayonet connector, a clamp device and a pin connection.

10. The probe assembly of claim 1, wherein:
    the connector assembly is attached to the probe sheath through a bayonet mount.

11. The probe assembly of claim 1, wherein:
    the probe sheath is a flexible, compressible sheath.

12. The probe assembly of claim 11, wherein:
    the locking mechanism is a locking key having a rigid linking member connecting the proximal end of the probe sheath to a distal end of the probe sheath, the rigid linking member preventing compression of the probe sheath.

13. The probe assembly of claim 12, wherein:
    the locking key is removable from the probe assembly to allow for compression of the probe sheath.

14. The probe assembly of claim 11, further comprising:
    a restraining key having a rigid linking member configured to connect the proximal end of the probe sheath to a connector attached to the vessel or tubing;
    wherein the rigid linking member prevents movement of the probe towards the proximal end of the probe assembly.

15. The probe assembly of claim 14, wherein:
    the rigid linking member further prevents further translational movement of the probe into the vessel or tubing.

16. The probe assembly of claim 15, wherein:
    the retraining key includes a first arm configured to contact a first mating portion of a connector attaching the probe assembly to the vessel or tubing, and second arm configured to contact a second mating portion of the connector.

17. A method of aseptically inserting a probe into a vessel or tubing, comprising the steps of:
    coupling a connector assembly to a probe sheath;

engaging a locking mechanism with a plunger received by the probe sheath to restrain axial movement of the plunger within the probe sheath;

inserting a probe through the plunger and into the probe sheath; and connecting the probe sheath to a port in the vessel or tubing via a connector assembly wherein the probe comprises the connector assembly attached to the distal end of the probe sheath, the connector assembly allowing for coupling of the probe sheath to the vessel or tubing; and a latch mechanism provided at a proximal end of the connector assembly.

18. The method according to claim 17, further comprising the step of:

disabling the locking mechanism; and advancing the probe through the probe sheath and the connector assembly such that a sensing portion of the probe is aseptically disposed within the vessel or tubing.

19. The method according to claim 18, further comprising the steps of:

advancing the probe includes longitudinally advancing the probe through the probe sheath until the latch mechanism is engaged, the latch mechanism restricting further forward or rearward movement of the probe with respect to the probe sheath.

20. The method according to claim 19, wherein:

engagement of the latch mechanism produces an audible click, indicating achievement of the predetermined distance of the distal end of the probe beyond the probe sheath.

21. A probe assembly for inserting a probe into a vessel or tubing, the assembly comprising:

a probe sheath having a proximal end and a distal end and being configured for operative coupling to a vessel or tubing, the probe sheath being configured to receive a probe and to permit movement of the probe towards the distal end of the probe sheath;

a connector assembly attached to the distal end of the probe sheath, the connector assembly allowing for coupling of the probe sheath to the vessel or tubing;

a plunger slidably received within the probe sheath, the plunger being configured to sealingly engage the probe sheath and the probe; and a latch mechanism provided at a proximal end of the connector assembly, configured to restrain movement of the probe with respect to the probe sheath after deployment of the probe into the vessel or tubing and to maintain a distal end of the probe a predetermined distance beyond the probe sheath.

22. The probe assembly of claim 21, wherein:

the latch mechanism provides an audible or tactile indication that the predetermined distance of the distal end of the probe beyond the probe sheath has been achieved.

23. The probe assembly of claim 21, wherein:

the latch mechanism includes at least one resilient arm positioned at a distal end of the probe sheath and a flange formed on a peripheral surface of the plunger;

wherein the at least one resilient arm is configured to engage the flange to restrain longitudinal movement of the plunger and probe towards the proximal end of the probe sheath.

24. The probe assembly of claim 21, further comprising:

a locking mechanism configured to restrain longitudinal movement of the probe with respect to the sheath in a locked state;

wherein the locking mechanism may be unlocked to allow for movement of the probe with respect to the sheath.

25. The probe assembly of claim 24, wherein:

the locking mechanism includes a clip having a detent that is configured to be received in a corresponding aperture in the plunger.

* * * * *